(12) United States Patent
Squires

(10) Patent No.: US 7,071,233 B2
(45) Date of Patent: *Jul. 4, 2006

(54) ANTIMICROBIAL PREVENTION AND TREATMENT OF HUMAN IMMUNEDEFICIENCE VIRUS AND OTHER INFECTIOUS DISEASES

(75) Inventor: Meryl Squires, Barrington Hills, IL (US)

(73) Assignee: Meryl J. Squires, Barrington Hills, IL (US)

( * ) Notice: Subject to any disclaimer, the term of this patent is extended or adjusted under 35 U.S.C. 154(b) by 348 days.

This patent is subject to a terminal disclaimer.

(21) Appl. No.: 10/084,759

(22) Filed: Feb. 26, 2002

(65) Prior Publication Data

US 2003/0104082 A1 Jun. 5, 2003

Related U.S. Application Data

(63) Continuation of application No. 08/824,041, filed on Mar. 26, 1997, now Pat. No. 6,350,784, which is a continuation-in-part of application No. 08/646,988, filed on May 8, 1996, now Pat. No. 6,355,684, which is a continuation-in-part of application No. 08/600,217, filed on Feb. 12, 1996, now Pat. No. 6,348,503, which is a continuation of application No. 07/595,424, filed on Nov. 13, 1991, now abandoned.

(51) Int. Cl.
*A61K 31/14* (2006.01)

(52) U.S. Cl. ............ 514/642; 514/28; 514/33; 514/53; 514/54; 514/456; 514/642; 514/643

(58) Field of Classification Search ........ 514/642, 514/643, 28, 33, 53, 54, 456
See application file for complete search history.

(56) References Cited

U.S. PATENT DOCUMENTS

| 4,797,420 A | * | 1/1989 | Bryant | 514/643 |
| 6,350,784 B1 | * | 2/2002 | Squires | 514/642 |
| 6,355,684 B1 | * | 3/2002 | Squires | 514/643 |

FOREIGN PATENT DOCUMENTS

| AU | 679162 | 2/1997 |
| DE | 3522075 A1 | 1/1987 |
| DE | 3533563 A1 | 3/1987 |
| EP | 308564 A1 * | 3/1989 |

OTHER PUBLICATIONS

Tyler, V.E., "The Honest Herbal, A Sensible Guide to the Use of Herbs and Related Remedies", 3rd Edition, pp. 115–117, 1993.*
Tyler, V.E., "The Honest Herbal, The Therapeutic Use of Pytomedicinals ", 3rd Edition, pp. 181–186, 1994.*
Abstract of EP 308564 A1 of Bourbon et al.*

* cited by examiner

*Primary Examiner*—Dwayne Jones
(74) *Attorney, Agent, or Firm*—Welsh & Katz, Ltd.; Thomas W. Tolpin

(57) ABSTRACT

An improved medical treatment and medicine is provided to quickly and safely resolve HIV and other microbial infections. The inexpensive medicine can be self administered and maintained for the prescribed time. The attractive medicine comprises an antimicrobial concentrate comprising microbe inhibitors, phytochemicals or isolates. Desirably, the effective medicine comprises a surfactant and an aqueous carrier or solvent and a nutrient. In the preferred form, the medicine comprises: *Echinacea* and *Commiphora myrrha* phytochemicals, benzalkonium chloride, a sterile water solution, and folic acid.

4 Claims, No Drawings

ANTIMICROBIAL PREVENTION AND TREATMENT OF HUMAN IMMUNEDEFICIENCE VIRUS AND OTHER INFECTIOUS DISEASES

RELATED APPLICATIONS

This application is a continuation-in-part of U.S. Ser. No. 08/824,041, filed on Mar. 26, 1997, now U.S. Pat. No. 6,350,784, which in turn is a continuation-in-part of U.S. Ser. No. 08/646,988, filed on May 8, 1996, now U.S. Pat. No. 6,355,684, which in turn is a continuation-in-part of U.S. Ser. No. 08/600,217, filed on Feb. 12, 1996, now U.S. Pat. No. 6,348,503, which in turn is a continuation-in-part of U.S. Ser. No. 07/595,424, filed on Nov. 11, 1990, abandoned on Nov. 13, 1991.

BACKGROUND OF THE INVENTION

The present invention relates to human immunedeficiency virus, and more particularly, to medical treatments and preventions for human immunedeficiency virus and other microbial infections.

It has been reported that there are currently about 22 million people infected with human immunodeficiency virus (HIV) throughout the world. The largest proportion of new HIV cases have originated in Africa and the Caribbean. The typical progression of HIV infection is divided into different stages: 1) viral transmission; 2) acute retroviral syndrome; 3) seroconversion; 4) a clinical latent period with or without persistent generalized lymphadenopathy (PGL); 5) early symptomatic HIV infection previously known as AIDS-related complex or ARC and more recently referred to as "B symptoms" according to the 1993 CDC classification); 6) acquired immune deficiency syndrome (AIDS) (AIDS indicator condition according to the 1987 CDC criteria and revised 1993 CDC criteria that include a CD4 cell count <200/mm$^3$); and 7) advanced HIV infection characterized by a CD4 cell count <50/mm$^3$. CD4 cells are lymphocytes targeted by HIV. In 1993 the CDC changed the definition of AIDS to include all patients with a CD4 count <200/mm$^3$; this definition includes patients in stages 4–7 regardless of symptoms.

The initial acute retroviral syndrome is accompanied by a precipitous decline in CD4 cell counts, high culturable plasma viremia, and high concentrations of HIV RNA in plasma. Clinical recovery occurs and high level HIV RNA plasma viremia is reduced with development of cytotoxic T lymphocyte (CPL) response. The CD4 cell count gradually declines over several years and then shows an accelerated decline at 1.5–2 years before an AIDS-defining diagnosis. HIV RNA concentrations in plasma are relatively stable until the HIV is in a late stage when the CD4 count is <200/mm$^3$ and the clinical course is characterized by infections, selected tumors, wasting, and neurologic complications. Generally, about 10% of patients develop an AIDS-defining diagnosis before the CD4 count decreases to 200/mm$^3$. The present median time to an AIDS-defining complication after the CD4 count is 200/mm$^3$ is 12–18 months. In the absence of therapy directed against HIV or PCP prophylaxis, the average time from viral transmission to an AIDS-defining diagnosis is about 10 years, and survival after an AIDS-defining complication was previously about one year.

The entire sequence of events for an average patient, in the absence of treatment directed against HIV, is approximately ten years from seroconversion to death. The median time from HIV seroconversion to AIDS has been reported to be about 7 years for transfusion recipients, 10 years for hemophiliacs, 10 years for drug users and 8–12 years for gay men. Rates of progression appear similar by sex, race, and risk category if adjusted for quality of care. For patients aged 16–24 years at seroconversion, the median time was 15 years; for those over 35 years at seroconversion, it was 6 years.

HIV infection can be acquired through sexual intercourse, from drug transfusions with contaminated blood, by drug addicts with infected needles, or by perinatal transmission. Symptomatic primary HIV infection, also referred to as an acute retroviral syndrome, has been reported in the preceding risk categories with a frequency of 50–90%. This syndrome has also been noted in seven of eight healthcare workers with HIV transmission following occupational exposure. The time from exposure to onset of symptoms is usually 2–4 weeks, but the incubation may be as long as six weeks. Typical symptoms are: fever, adenopathy, pharyngitis, rash comprising erythematous maculopapular with 5–10 mm lesions on the face and trunk, sometimes extremities including palms and soles or mucocutaneous ulceration on the mouth, esophagus or genitals, myalgias or arthralgias, diarrhea, headache, hepatosplenomegaly, thrush, nausea and vomiting. Neurologic symptoms can include: meningoencephalitis, peripheral neuropathy, facial palsy, Guillain-Barre syndrome, brachial neuritis, radiculopathy, cognitive impairment, and psychosis. The acute illness is generally accompanied by high level HIV viremia with p24 antigenemia, plasma viremia, and high titers of HIV in peripheral blood mononuclear cells.

The cytotoxic T lymphocyte (CTL) response is first and usually precedes detectable humoral response by several weeks. CTL response is accompanied by a 3–5 log decrease in HIV concentration in peripheral blood. The high level of viremia during this acute phase of the illness may be associated with dissemination of the virus to the CNS and lymphatic tissue. Lymph tissue serves as the major reservoir of HIV burden and replication. Infection of non-lymphoid organs with high levels of HIV appears to occur in late-stages of HIV.

The presence of symptoms rather than asymptomatic seroconversion as well as a prolonged illness greater than 14 days appear to correlate with more rapid progression to AIDS. Seroconversion with positive HIV serology generally takes place at 6–12 weeks following transmission such as by transfusion or needles injury to a healthcare worker. The median interval is 63 days. The CTL response is associated with a sharp reduction in quantitive viral load in blood, clinical recovery from the acute retroviral syndrome and return of the CD4 cell count to higher levels that are often in the normal range for most laboratories.

The HIV patient becomes clinically asymptomatic and generally has no findings on physical exam except for Persistent Generalized Lymphadenopathy (PGL) comprising enlarged lymph nodes. Studies of lymph nodes show high concentrations of HIV as extracellular virus trapped on the follicular dendritic cell processes within germinal centers and as intracellular virus predominantly in latent form. The lymph tissue serves as a major reservoir for HIV, the follicular dendritic cells filter and trap free virus and infected CD4 cells, and the viral burden in peripheral blood mononuclear cells is relatively low. With progressive disease, the lymph node configuration is disrupted by HIV.

Virologic studies in patients with asymptomatic HIV infection show high rates of HIV replication with production of an average of 10$^9$ virions daily. Viral replication is accompanied by massive destruction and the production of $10^9$ CD4 cells daily. The turnover of CD4 cells represents 6–7% of the total body CD4 cells so that the entire supply turns over every 15 days. AIDS has been considered a consequence of continuous, high-level replication of HIV-1, leading to virus and immune-mediated termination of CD4 lymphocytes.

Advanced HIV Infection occurs in patients with a CD4 cell count of <50/mm$^3$. These patients have limited life expectancy with a median survival of 12–18 months. Virtually all patients who die of HIV-related complications are in this CD4 cell count stratum.

The Food & Drug Administration (FDA) has approved many reverse transcriptase (RT) inhibitors. RT enzymes convert viral RNA into DNA. RT inhibitors can interrupt this process. The RT inhibitor AZT, which is sold under the brand names of Retrovir and zidovudine by Glaxo Wellcome, was approved by the FDA in 1987. The RT inhibitor ddl, which is sold under the brand names of Videx and didanosine by Bristol-Myers Squibb, was approved by the FDA in 1991. The RT inhibitor ddC, which is sold under the brand names of HIVID and dideoxycyytidine by Hoffman-LaRoche, was approved by the FDA in 1992. The RT inhibitor d4T, which is sold under the brand names of Zerit and stavudine by Bristol-Myers Squibb, was approved by the FDA in 1994. The RT inhibitor 3TC, which is sold under the brand names of Epivir and lamivundine by Glaxo Wellcome, was approved by the FDA in 1995. The TR inhibitor Nevirapine, which is sold under the brand name of Viramune by Boehringer Ingelheim, was approved by the FDA in 1996.

The Food & Drug Administration (FDA) has now approved three protease inhibitors for the treatment of human immunedeficiency virus (HIV) infection. Saquinavir sold under the brand name of Invirase by Hoffinan-LaRoche Laboratories, was the first protease inhibiting agent to be approved by the FDA. Ritonavir, another protease inhibitor, which is sold under the brand name of Norvir by Abbott Laboratories, received FDA approval in March, 1996 as did Indinavir sold under the brand name of Crixivan by Merck & Co.

Protease inhibitors have a different mechanism of action from that of previously approved anti-HIV drugs, such as the nucleoside analogues AZT and 3TC sold under the brand names of zidovudine and lamivundine by Glaxo Wellcome, ddl and d4T sold under the brand names didanosine and stavudine by Bristol-Myers Squibb, and ddC sold under the brand name of dideoxycytidine by Roche Laboratories. Protease inhibitors block the enzyme which HIV requires for the completion of its replication cycle and formation of viable new viruses. Without the protease enzyme, viral structural proteins cannot be manufactured properly, and faulty, non-infectious virus is formed. The nucleoside analogues block a different enzyme-reverse transcriptase. This action can prevent viral RNA from producing viral DNA which can then incorporate into the DNA of human cells. Combining one or more reverse transcriptase inhibitors with a protease inhibitor, sometimes referred to as a "cocktail," is claimed to attack HIV replication at two points in the replication cycle. Clinical trials combining saquinavir with AZT, ddC, or both demonstrate a greater decline in the number of HIV particles in the blood, sometimes referred to as viral burden, and a grater increase in CD4 cells (T lymphocytes) than previously observed with reverse transcriptase inhibitors alone. Sometimes, the cocktails have been toxic and ineffective for some patients. Clinical benefit in terms of improved survival or reduced disease progression rate, however, has not yet been fully demonstrated for combination (cocktails) of RT inhibitors and protease inhibitors. Physicians, however, are starting to consider HIV a chronic manageable disease rather than a death sentence.

Saquinavir protease inhibitors have been approved by the FDA for use in combination with reverse transcriptase inhibitors in patients with advanced AIDS. Saquinavir protease inhibitors may be tolerated by some patients without the hematologic or neurologic toxicities encountered with the nucleoside analogues. Certain prescription drugs including rifampin, rifabutin, phenobarbital, dilantin, and dexamethasone, may significantly decrease plasma levels of saquinavir protease inhibitors and should be avoided in patients taking saquinavir. Viral resistance to saquinavir protease inhibitors, as with other anti-HIV drugs has been reported.

Ritonavir and indinavir protease inhibitors appear to be more potent against HIV than the current formulation of saquinavir. Ritonavir protease inhibitors require refrigeration. Ritonavir protease inhibitors are currently used in combination with nucleoside analogues (drugs like AZT) or as monotherapy. An early study treated 32 patients with ritonavir plus AZT plus ddC. After 20 weeks, median CD4 cell counts rose from 83 cells/mm$^3$ at baseline to 106 cells/mm$^3$. Viral load, a measure of the number of viral copies in the blood, decreased by almost 100-fold. Ritonavir is dosed at 600 mg orally twice a day, which can require twelve capsules each day. The drug is available in 100 mg capsules. Side effects are fairly common, including: gastrointestinal symptoms with nausea, vomiting, and diarrhea. Other side effects include numbness and tingling, particularly around the mouth, and liver inflammation comprising a form of hepatitis.

Indinavir protease inhibitors received accelerated FDA approval based on studies demonstrating mean rises in CD4 counts of about 100 cells/mm$^3$ and drops in viral load of almost 100-fold with a combination of AZT plus 3TC plus indinavir. Indinavir is dosed at 800 mg orally three times per day (2 capsules 3, times daily). In contrast to ritonavir, indinavir can be taken on an empty stomach to improve absorption. Indinavir causes fewer gastrointestinal side effects than ritonavir and seems to be better tolerated overall by some patients. The major side effect of Indinavir protease inhibitors are the development of kidney stones. The drug is partially excreted in the urine and it can crystallize to form stones if adequate hydration is not maintained. Indinavir protease inhibitors can also affect the liver, causing a rise in blood levels of bilirubin, i.e., a bile pigment formed from the breakdown of red blood cells. Indinavir protease inhibitors can also cause drug interactions.

Analysis of resistance to protease inhibitors has not been fully determined. Saquinavir and ritonavir protease inhibitors can currently cost the patient approximately U.S. $600 per month. Indinavir protease inhibitors is priced about 30% below this level. A three-drug combination of AZT plus 3TC plus ritonavir protease inhibitors can cost a patient over U.S $1,000/month. Combinations (cocktails) of RT inhibitors and protease inhibitors can cost as much as $25,000 per year. Although, protease inhibitors may be helpful, the medical community and society have not yet resolved patient cost problems for these expensive drugs.

Herpes simplex virus (HSV) commonly referred to as "herpes virus" or "herpes," is an infectious disease which also has reached crisis proportions nationally with estimated numbers of infected people at 70%–80% of our population as reported by the American Societal Health Association (ASHA) and growing annually by 500,000 people. There are two common types of herpes: herpes simplex virus 1 (HSV 1) and herpes simplex virus 2 (HSV 2). Herpes enters the human body through minuscule breaks in the epidermal tissue usually by contact with an infected host and is marked by eruption of one or more vesicles, usually in groups, following an incubation period of approximately four days. Typically the course of the infectious outbreak initiates with the prodromal stage; advancing to vesicular eruption; followed by ulceration; coalescing; resolution; and the latency period. The outbreak can last for several weeks and on average lasts two-three weeks. In some immune compromised individuals the outbreak can last for months. The vesicles can appear anywhere on the skin or mucosa, typically appearing on the lips as cold sores, glands, oral mucosa, conjunctiva and cornea, genitalia, anal mucosa and peri-anal tissue.

Herpes symptoms include: inguinal swelling, pain, fever, malaise, headaches, muscle aches, and swollen glands. Some individuals who have the trigeminal nerve compromised with oral herpes, have excruciating facial pain, difficulty swallowing, eating and facial swelling. Individuals with the sacral nerve affected have severe upper leg pain, swelling, and great difficulty walking.

Herpes simplex virus (HSV) infection is recrudescent, residing in the nerve ganglia, then recurring due to some, as yet unknown, stimulus. Recurrent herpetic infections can be precipitated by almost anything, including: overexposure to sunlight; nutritional deficiencies; stress, menstruation; immunosuppression; certain foods; drugs; febrile illness; etc. Recently herpes virus was isolated from cardiac tissue.

HSV 1 and HSV 2 infections pose very serious health threats often causing: blindness; increased cancer risk of the cervix; aseptic meningitis and encephalitis; neonatal deaths; viremia; etc. The devastating effects of this disease, go well beyond the medical scope of human suffering. HSV is responsible for serious psychological and emotional distress as well as substantial economic loss to the nation and the world.

Various treatments for herpes have been proposed and have included topical application of such agents as povodone-iodine, idoxuridine, trifluorothymidine, or acyclovir. Such treatments have met with varying degrees of success. Most prior treatments have proven disappointing. Acyclovir, taken orally for systemic treatment of HSV, is somewhat effective. However, acyclovir is only successful in interrupting the replication of the virus. It is not successful in treating an infectious outbreak either systemically or topically. Strains resistant to acyclovir have been reported. Individuals with Auto Immune Deficiency Syndrome (AIDS) are seriously immune-compromised and suffer especially debilitating outbreaks of HSV. Additionally, AIDS individuals may carry acyclovir resistant strains of HSV, which can make acyclovir ineffective for these individuals.

It is, therefore, desirable to develop a safe and successful medical treatment to help treat and prevent the very serious problems of HIV and other infectious diseases.

SUMMARY OF THE INVENTION

An improved medical treatment and medicine are provided which, when administered systemically, inhibits the attachment of human immunedeficiency virus (human immunodeficiency virus) (HIV) to target cells and prevents the spread of HIV. Advantageously, use of the novel medical treatment and medicine can be helpful to prevent the sexual transmission of HIV and other viruses. Significantly, the improved medical treatment and medicine are safe, less expensive and effective.

The improved medicine, also referred to as Viracea 2 HIV-4, comprises a novel medical composition, formulation, antimicrobial compound and solution. The new antimicrobial medical treatment and microbicidal medicine are successful in treating primarily HIV systemically and can be useful in treating other microbial infections including, but not limited to: varicella zoster virus (herpes zoster) and cytomegalovirus. In some circumstances, it may be desirable to use the novel medicine topically.

While the novel medicine and antimicrobial compound is particularly useful in dramatically inhibiting human immunedeficiency virus infection (HIV), it may be useful in treating other microbial diseases (microbe-causing diseases) such as: Epstein barr, papilloma virus, cellulitis, staphylococci, streptococci, mycobacteria, influenza, parainfluenza, adenoviruses, encephalitis, meningitis, arbovirus, arenavirus, anaerobic bacilli, picornavirus, coronavirus and synsytialvirus, as well as herpes simplex virus, varicella zoster virus and cytomegalovirus.

While the medical treatment and medicine is particularly useful for inhibiting HIV and other infectious diseases in persons (human beings) (homo sapiens), they can also be useful for veterinary purposes for treating viral and bacterial infections and infectious diseases in animals, such as: dogs, cats, birds, horses, cows, sheep, swine (pigs and hogs), and other farm animals, as well as rodents and other animals seen in zoos.

Advantageously, the improved medical treatment and medicine of the present invention yielded unexpected, surprisingly good results. This easy to use microbicide solution can provide immediate absorption in parenteral administration. Upon administration, there can be a slight tingling effect. Within minutes of application, a slight medicinal taste in the mouth may be experienced. Initial, in vitro testing of the novel medical treatment and medicine demonstrated extremely surprising inhibitory effects on HIV virus. Desirably, the novel medicine is made from readily available, over the counter (OTC) chemicals or products and provides a safe comfortable, and economical treatment.

Desirably, the novel medicine (medical composition) includes microbe inhibitors which inhibit, suppress and stop microbial infections from microbe-causing diseases. The microbe inhibitors comprise antimicrobial isolates, botanical extracts or phytochemicals, of at least a portion of one or more of the special plants listed below. The microbe inhibitors can comprise viral inhibitors to inhibit viral diseases, such as: HIV, herpes simplex virus 1 (HSV 1), herpes simples virus 2 (HSV 2), varicella zoster virus (herpes zoster), cytomegalovirus, epstein barr, papilloma virus, viral influenza, viral parainfluenza, adenovirus, viral encephalitis, viral menigitus, arbovirus, arenavirus, picornavirus, coronavirus, and synstialvirus. The microbe inhibitors can also comprise bacterial inhibitors to inhibit bacterial diseases, such as: cellulitis, staphylocci, streptoci, mycolbacteria, bacterial encephalitis, bacterial meningitis, and anaerobic bacilli. In some circumstances, the microbe inhibitors can include fungi inhibitors.

Better results may be obtained if *Echinacea* and *Commophora* (also referred to as *Commiphora*) or other plants are not used in the medicine in their raw, untreated and uncut state. For even better results, the medicine may exclude: Arabinose, betaine, cellulose, copper, fructose, fatty acids, galactose, glucose, iron, potassium, protein, resin, sucrose, and xylose.

The improved medical treatment provides a novel method and process for use in treating the above infectious diseases. For some infectious diseases, the microbial inhibitors can be applied and maintained on the microbial infected on the infected area (region or surface) until the external symptoms and physical manifestations of the infection disappear, reside or resolve about the infected area. The medicine can be administered by syringe injection, sublingual intramural, spraying, dabbing, dusting, swabbing, sponging, brushing, pouring, dispensing, covering, or heavily coating the medicine the microbial infected areas, such as: lymph nodes, lymphatic system, T-cells, oral mucosa, nasal mucosa, vagina tissue, labial tissue, rectal tissue, anal tissue, perianal tissue, lips, cutaneous tissue, ocular tissue, conjunctiva, and eyelids.

Preferably, the microbial inhibitors or antimicrobial compound is applied systemically with a syringe into the rectal canal or vagina to treat or prevent the sexual transmission of HIV. The microbial inhibitors or antimicrobial compound can be applied in the preceding manner 4–20 times per day for 4 to 18 consecutive days to substantially decrease the viral load of patients infected with HIV, i.e., to decrease the amount of HIV and AIDS virus in the body.

Preferably, the improved medicine, medical composition or microbial compound is a phytochemical concentrate which is combined and simultaneously or concurrently applied with a surfactant, a nutrient, and a carrier, solvent or diluent to provide a microbicide medicinal solution. The nutrient serves as a catalyst, activator, phytochemical initiator, nutritional supplement, and auxiliary carrier. The nutrient can comprise one or more of the following: a water soluble vitamin, a fat soluble vitamin, vitamin A, vitamin B complex, (B vitamin complex), vitamin D, vitamin E, vitamin K, vitamin B1, vitamin B2, vitamin B5, vitamin B6, vitamin B12, vitamin B15, and preferably folacin or folic acid.

To this end, the interesting microbicide solution comprises an antimicrobial detergent surfactant, with botanical extracts. The surfactants preferably are cationic surfactants which can comprise singly or any number of quaternary ammonium chlorides having 6–18 carbons such as alkylbenzyldimethylammonium chloride, mixtures of alkylbenzyldimethylammonium chloride, alkyldimethyl/ethylbenzylammonium chloride, n-alkyldimethylbenzylammonium chloride, diisobutylphenoxyethoxyethyldimethylbenzylammonium chloride, N—($C_{12}C_{14}C_{16}$) dimethylbenzylammonium chloride, benzalkonium chloride, octyldecyldimethyloammonium chloride, didecyldimethylammonium chloride, dioctyldimethylammonium chloride, dialkyldimethylammonium chloride, dialkylmethylbenzylammonium chloride, octyldecyldimethylammonium chloride, dimethylbenzylammonium chloride, laurryldimethylb enzylammonium chloride, o-benzyl-p-chlorophenol, dideryldimethylammonium chloride, doctyldimethylammonium chloride, alkyl ($C_{14}C_{12}C_{16}$) dimethylbenzylammonium chloride, and preferably comprises alkylbenzyldimethylammonium chloride most preferably benzalkonium chloride. The range of activity of the cationic surfactant can be 5% to 90% but for best results 8% to 20%. Quaternary ammonium salts are readily available commercially. In some circumstances it may be useful to use other surfactants, such as, but not limited to: DMSO, glycolic acid surfactants, enzyme surfactants, ampholytic surfactants, switterionic surfactants, and carotene, garlic oil, camphor oil, soluble vitamins, soluble minerals, rape seed oil, nut oils, olive oil, liposomes, ascorbic acid, evening primrose oil, pycnogenol, grape seed oil, lanolin, Ethocyn, collagen, aloe vera, bee pollen, royal jelly, chondroitin sulfate A, sea vegetables, EDTA, fatty acids, herbs, lecithin, bioflavinoids, grain oils or powders, algae, teas, vinegars, acidophilus, cell salts, ascorbic acids, hydra 5, glandulars, amino acids, psyllium, plant derivatives, or other sterile carriers.

The botanical extracts antimicrobial isolates or phytochemicals contained in this new medicine and medical treatment can be comprised of: myrrha gum resin, sequiterpenses, curzenone, dihydro fuanodien-6-one, 2-methoxylfurandiene, elemol, acetic acid, alpha-amyrone, arabinose, alpha-bisabolene, gamma-bisabolene, cadinene, campesterol, cholesterol, cinnamaldehyde, commiferin, alpha-commiphoric acid, beta-commiphoric acid, gama-commiphoric acid, commiphorinic acid, m-cresol, cumic alcohol, cuminaldehyde, dipentene, elemol, 3-epi-alpha-arnyrin, eugenol, furanodiene, furanodienone, galactose, gum, heerabolene, alpha-heerabomyrrhol, beta-heerabomyrrhol, heeraboresene, limonene, 4-0-methyl-glucuronic acid, n-nonacesane, beta-sitosterol, xylose, caropylenes (carophylenes), lynderstyrene (lindestyrene), arabinose, betaine, copper, echinacen, echinacin B, echinacoside, echinolone, enzymes, fructose, fatty acids, galactose, glucose, glucuronic acid, inulin, inuloid, iron, pentadecadiene, polyacelylene compounds; polysaccharides, such as, but not limited to, arabinogalactan; potassium, protein, resin, rhamnose, sucrose, sulfur, tannins, vitamins a, c, and e, alkylamides, apigenin, arabinogalacta, ascorbic acid, behenic-acid-ethyl-acid, betaine, borneol, bornyl-acetate, caffeic-acid, 2-0-caffeoyl-3-(5-alpha carboxybeta) 3,4 dihydroxyphenyl, 2-0-caffeoyl-3-0 cumaroyltaraic acid, 6-0-caffeoylechinacoside, 2-0-caffeoyl-3-0-feruloyltartaric acid, 2-0-caffeoyltartaric acid, calcium, carbonate, beta carotene, carophyllene, carophyllene-epoxide, chloride, chlorgenic acid, cichoric acid, cichoric-acid-methyl-ester, cobalt, cyanadin-3-0-(beta-d-glycopyranoside), cynadin-3-(6-0-malonyl beta-d-glycopyranoside), cynarin, deca (2e,4e,6e) trienoic acid-isobutylamide, des-rhamnosylverbascoside, 3,5-dicaffeoylquinic acid, 4-5-0 dicaffeoylquinic acid, 2,3-0-diferuloltartaric acid, do-deca-(2e,4e)-dienoic acid-isobutylamide, dodeca-2,4-dien-1-yl isovalerate, dodeca (2e,6z,8e,10e)-tetraenoic acid-isobutylamide, epishobunol, beta-farnesene, 2-0-feruloytartaric acid, germacrene, heptadeca-(8z,11z)-dien-2-one, heteroxylan, humulene 8-12, (e)-10-hydroxy-4,10-dimethyl 4,11-calcium, carbonate, beta carotene, carophyllene, carophyllene-epoxide, chloride, chlorgenic acid, cichoric acid, cichoric-acid-methyl-ester, cobalt, cyanadin-3-0-(beta-d-glycopyranoside), cynadin-3-(6-0-malonyl beta-d-glycopyranoside), cynarin, deca (2e,4e,6e) trienoic acid-isobutylamide, des-rhamnosylverbascoside, 3,5-dicaffeoylquinic acid, 4-5-0 dicaffeoylquinic acid, 2,3-0-diferuloltartaric acid, do-deca-(2e,4e)-dienoic acid-isobutylamide, dodeca-2,4-dien-1-yl isovalerate, dodeca (2e,6z,8e,10e)-tetraenoic acid-isobutylamide, epishobunol, beta-farnesene, 2-0-feruloytartaric acid, germacrene, heptadeca-(8z,11z)-dien-2-one, heteroxylan, humulene 8-12, (e)-10-hydroxy-4,10-dimethyl 4,11-dodecadien-2-one, 13-hydroxyoctadeca-(9z,11e,15z)-trienoic-acid, inulin, iron, isochlorogenic acid, isorhamnetin-3-rutinoside, isotussilagine, kaempferol, kaempferol-3-glucoside, kaempferol-3-nutinoside, limonene, luteolin, luteolin-7-glucoside, magnesium, manganese, 2-methyltetradeca-5,12 diene, 2-methyltetradeca-6,12 dience, methyl-p-hydroxycinnamate, marcene, niacin, palmitic acid, pentadeca-(8z,11z)-dien-2-one, pentadeca-(8z,13z)-dien- 11-lyn-2-one, pentadeca-8-en-2-one, pentadeca-(8z)-en 2 one, pentadeca-(8z)-en-11,13 dien-2-one, 1-pentadecene, penta-(1,8z)-diene, phosphorous, alpha pinene, beta pinene, polyacetylenes, pontica epoxide, potassium, protein, quercetagetin-7-glucoside, quercetin, quercetin-3-galactoside, quercetin-3-glucoside, quercetin-3-robinoside, quercetin-3-xyloside, quercetin-3-xylosylgalactoside, rhamnoarabinogalactan, riboflavin, rutin, rutoside, selenium, silicate, beta-sitosterol, sitosterol-3-beta o-glucoside, sodium, stigmasterol, sulfate, tartaric acid, tetradeca-(8z)-en-11,13 dien-2-one, thiamin, n-triacontanol, trideca-1-en-3,5,7,9,10-pentayne, tussilagine, vanallin, verbascoside. For better results, the phytochemical concentrates include the above phytochemicals, excluding Arabinose, bataine cellulose, copper, fructose, fatty acids, galactose, glicose, iron, potassium, protein, resin, sucrose, and, xylose.

The botanical extracts, antimicrobial isolates and phytochemicals maybe separated, extracted and isolated from portions of plants, such as: *pimpinella anisum*, myroxylon, arctostaphylos, carum, capsicum, *eugenia mytacea*, coriandrum, inula, allium, gentiana, juniperus, calendula, origanum, *mentha labiate*, commiphora, plantago, rosmarinus, ruta, lamiaceae, meliosa, baptisa, artemisa, sage, mentha, *parthenium integrifolium*, eucalyptus, asteriacea, and preferably: (1) from the genus *Echinacea* of the family Astericaea, namely, *Echinacea purpurea, Echinacea angustofolium, (Echinacea pallidae), Echinacea vegetalis, chinacea atribactilus* and their *Echinacea pallidum* and cultivars; as well as from the genus *Commophora*, namely, *Commophora myrrha, Commophora molmol, Commophora erythraea*, and their cultivars. For best results, the phytochemicals and antimicrobial isolates are extracts from *Echinacea purpurea, Echinacea angustifolium* and *Commophora myrrha*.

The inventive technology, treatment and medicine yield very attractive, unexpected, surprisingly good and consistent results. Tests show the microbicide solution (medicine) and medical treatment to be extremely useful to: control HIV infection, inhibit attachment of virus to target cells, act as a preventive microbicide, extend the latency periods of HIV and other diseases, and dramatically inhibit HIV and other viruses, while being generally safe to the patient and the environment.

A more detailed explanation of the invention is provided in the following description and appended claims.

DETAILED DESCRIPTION OF THE PREFERRED EMBODIMENTS

A microbicide and treatment are provided to inhibit human immunedeficiency virus, also referred to as human immunodeficient virus or HIV. Desirably, the HIV microbicide and treatment completely inhibits HIV, as well as other infectious microbial diseases, and are safe and non-toxic to humans, animals, and the environment.

The HIV microbicide and medicine can comprise a surfactant and an herbaceous botanical providing a botanical extract, phytochemical, antimicrobial isolate, anti-viral isolate, microbe inhibitor, and viral inhibitor. The preferred microbicide composition can comprise: a surfactant; an aqueous diluent; a nutrient; and the herbaceous botanical of the genus *Echinacea* (E), of the family Asteracea, species: *purpurea, angustifolia, pallidae, vegetalis, atribactilus* and the cultivars, as well as the herbaceous botanical of the genus *Commiphora* species: *Commiphora myrrha, Commiphora molmol, Commiphora erythraea*, and their cultivars. Preferably, the herbanaceous botanicals are extracts and isolates comprising *Commiphora* phytochemicals and *Echinecea* phytochemicals as found in and extracted from *Commiphora myrrha, Echinacea purpurea, Echinacea pallidae*, and *Echinacea angustofolia*. For best results, the medical treatment and microbicide (medicine) comprises: a cationic surfactant; the phytochemicals from *Echinacea purpurea, Echinacea angustofolia*; and *Commiphora myrrha* a sterile aqueous diluent and folacin. The ratio of *Commiphora myrrha* to *Echinecea purpurea* and *Echinecea augustofolio* preferably ranges from 1:2 to 1:4.

The surfactant provides a certain debridement at the cellular surface level with a broad spectrum of antimicrobial action. Surfactants of this nature can comprise quaternary ammonium salts containing 6–18 carbon atoms. Preferably the quaternary ammonium salt surfactant, is a mixture of alkyl dimethylbenzylammonium chlorides, which can be: benzalkonium halide, benzalkonium bromide, benzalthonium chloride and most preferably benzalkonium chloride. The HIV treatment can comprise a 100% active aqueous solution but can also be used in concentrate. The solution can comprise by weight various concentrations of surfactants such as 0.005% to 0.8%, preferably 0.02% to 0.30% and most preferably 0.02% to 0.26%.

The phytochemicals in the botanical Echinacea have demonstrated impressive activity against bacteria, viruses, and some fungi. The exact mechanism is unknown. When the inventive microbicide was tested topically on HIV and HSV 1 & 2, it is effective in treating herpes simplex infectious outbreaks. When tested in vitro, it showed inhibitory activity against HIV-1 and HSV 1 & 2.

The phytochemical concentrate composition comprises the following isolated constituents, botanical extracts, microbial inhibitors, and antimicrobial isolates: polysaccharides, echinacen, echinaceine, echinacoside (caffeic acid ester), echinolone, echinadiol, enzymes, glucuronic acid, inuloid, pentadecadiene, polyacelylene compounds, arabinogalactan, rhamnose, PS I (a 4-0-methylglucoronoarabinoxylan, $M_r$ 35 kD) and PS II (an acid rhamnoarabinogalactan, $M_r$ 450 kD), cynarin (1,5-di-0-caffeoylquinic acid), chicoric acid (2,3-0-di-caffeoyltartaric acid) and derivatives, alkylamides, keto-alkynes and -alkenes; quinones; oils including: borneol, bornyl acetate; pentadeca-8(z)-en-2-one, germacrene D; caryophyllene; caryophyllene epoxide; anthocyanins pyrrolizidine alkaloids; lipophilic amides, isobutylamides; polyacetylenes; myrrha gum resin; curzerenone (furahoeudesmane type); dihydro fuanodien-6-one; 2-methoxyfuranodiene (furanoelemene type); elamol; lyndestyrene (furanogermacrane type); alkylamides, apigenin, arabinogalacta, ascorbic acid, behenic-acid-ethyl-acid, betaine, borneol, bornyl-acetate, caffeic-acid, 2-0-caffeoyl-3-(5-alpha carboxybeta) 3,4 dihydroxyphenyl, 2-0-caffeoyl-3-0 cumaroyltaraic acid, 6-0-caffeoylechinacoside, 2-0-caffeoyl-3-0-feruloyltartaric acid, 2-0-caffeoyltartaric acid, calcium, carbonate, beta carotene, carophyllene, carophyllene-epoxide, chloride, chlorgenic acid, cichoric acid, cichoric-acid-methyl-ester, cobalt, cyanadin-3-0-(betad-glycopyranoside), cynadin-3-(6-0-malonyl beta-d-glycopyranoside), cynarin, deca (2e,4e,6e) trienoic acid-isobutylamide, des-rhamnosylverbascoside, 3,5-dicaffeoylquinic acid, 4-5-0 dicaffeoylquinic acid, 2,3-0-diferuloltartaric acid, do-deca-(2e,4e)-dienoic acid-isobutylamide, dodeca-2,4-dien-1-yl isovalerate, dodeca (2e,6z,8e,10e)-tetraenoic acid-isobutylamide, epishobunol, beta-farnesene, 2-0-feruloytartaric acid, germacrene, heptadeca-(8z,11z)-dien-2-one, heteroxylan, humulene 8-12, (e)-10-hydroxy-4,10-dimethyl 4,11-dodecadien-2-one, 13-hydroxyoctadeca-(9z,11e,15z)-trienoic-acid, inulin, iron, isochlorogenic acid, isorhamnetin-3-rutinoside, isotussilagine, kaempferol, kaempferol-3-glucoside, kaempferol-3-nutinoside, limonene, luteolin, luteolin-7-glucoside, magnesium, manganese, 2-methyltetradeca-5,12 diene, 2-methyltetradeca-6,12 dience, methyl-p-hydroxycinnamate, marcene, niacin, palmitic acid, pentadeca-(8z,11z)-dien-2-one, pentadeca-(8z,13z)-dien-11-lyn-2-one, pentadeca-8en-2-one, pentadeca-(8z)-en 2 one, pentadeca-(8z)-en-11,13 dien-2-one, 1-pentadecene, penta-(1,8z)-diene, phosphorous, alpha pinene, beta pinene, polyacetylenes, pontica epoxide, potassium, protein, quercetagetin-7-glucoside, quercetin, quercetin-3-galactoside, quercetin-3-glucoside, quercetin-3-robinoside, quercetin-3-xyloside, quercetin-3-xylosylgalactoside, rhamnoarabinogalactan, riboflavin, rutin, rutoside, selenium, silicate, beta-sitosterol, sitosterol-3-beta o-glucoside, sodium, stigmasterol, sulfate, tartaric acid, tetradeca-(8z)-en-11,13 dien-2-one, thiamin, n-triacontanol, trideca-1-en-3,5,7,9,10-pentayne, tussilagine, vanallin, verbascoside, sequiterpenes; acetic acid, alpha-amyrone, arabinose, alpha-bisabolene, gamma-bisabolene, cadinene, campesterol, cholesterol, cinnamaldehyde, commiferin, alpha-commiphoric acid, beta-commiphoric acid, gama-commiphoric acid, commiphorinic acid, m-cresol, cumic alcohol, cuminaldehyde, dipentene, elemol, 3-epi-alpha-amyrin, eugenol, furanodiene, furanodienone, galactose, gum, heerabolene, alpha-heerabomyrrhol, beta-heerabomyrrhol, heeraboresene, limonene, 4-0-methyl-glucuronic acid, n-nonacesane, beta-sitosterol, xylose, caropylenes (carophylenes), myrrha gum resin, curzenone, dihydro fuanodien-6-one, and 2-methoxyfurandiene.

For best results, the antimicrobial isolates of the phytochemical concentrate comprise by weight (based upon the total weight of the inventive medical composition): 0.3–9% echinacoside; 0.1–7% PS I (a 4-0-methylglucoronoarabinoxylan, M™ 35 kD) and PS II (an acid rhamnoarabinogalactan, M™ 450 kD); 0.1–10% cynarin (1,5-di-0-caffeoylquinic acid) and chicoric acid (2,3-0-di-caffeoyltartaric acid) and derivatives; 0.2–4% echinolone; 0.2–8% echinacin B; 0.1–6%; echinaceine; 0.2–7% anthocyanins comprising cyanidin 3-0-β-D-glucopyranoside and 3-0-(6-0-malonyl-β-D-glucopyranoside); 0.01–0.06% pyrrolizidine alkaloids comprising tussilagine and isotussilagine; 0.003–0.009% isomeric dodeca isobutylamides and 2E,4E,8Z 10E/Z-tetraenoic acid; 0.01–2% caryopylenes; as well as *Commophora* myrrh phytochemicals comprising: myrrha gum resin, curzenone, dihydro fuanodien-6-one, 2-methoxyfurandiene, lynderstyrene (lindestrene) sequiterpenes, acetic acid, alpha-amyrone, arabinose, alpha-bisabolene, gamma-bisabolene, cadinene, campesterol, cholesterol, cinnamaldehyde, commiferin, alpha-commiphoric acid, beta-commiphoric acid, gama-commiphoric acid, commiphorinic acid, m-cresol, cumic alcohol, cuminaldehyde, dipentene, elemol, 3-epi-alpha-amyrin, eugenol, furanodiene, furanodienone, galactose, gum, heerabolene, alpha-heerabomyrrhol, beta-heerabomyrrhol, heeraboresene, limonene, 4-0-methyl-glucuronic acid, n-nonacesane, beta-sitosterol, xylose, caropylenes (carophylenes), and lynderstyrene (lindestyrene).

The phytochemical concentrate can comprise by weight: 2%–90% of the medical composition and solution and preferably comprises not less than 15% of the composition and solution; and for best results, comprises 40%–60% of the medical composition and solution.

The diluent dissolves the benzalkonium chloride (surfactant) and phytochemical concentrates and can act as a carrier in sprays, tubes, and dropper bottles. The preferable diluent is an aqueous diluent and most preferably is a sterile aqueous diluent. The ratio of water in the aqueous solution to benzalkonium chloride can range from 30,000:1 to 250:1 and preferably from 5000:1 to 750:1. The ratio of water to the combined concentrates of benzalkonium chloride and phytochemicals can comprise a range of 2:1 to 100:1 with a preferable range of 4:1 to 40:1, and for best results can comprise a ratio of 6:1 to 20:1.

For best results, the improved microbicidal treatment and medicine (microbicide) for herpes, comprises by weight: 0.02% to 0.3% benzalkonium chloride and to avoid toxicity preferably less than 0.26%; 40% to 60% *Echinacea* and *Commophora* phytochemicals; 0.01% to 25% most preferably 2% to 12% nutrient; and 20% to 60%, most preferably 29.74% to 59.8% sterile water. The medicine (microbicide) desirably comprises a vitamin nutrient which serves as a nutritional carrier and provides a synergistic effect when combined with *Commophora myrrha, Echinecea purpurea* and *Echinecea angustofolic*. The nutrient can comprise one or more of the following: vitamin A, vitamin B complex, vitamin D, vitamin E, vitamin K, a water soluble vitamin, a fat soluble vitamin, vitamin B1, vitamin B2, vitamin B5, vitamin B6, vitamin B12, vitamin B15, and preferably folacin or folic acid.

While water is the preferred diluent and aqueous carrier, it may be desirable in some circumstances to use other carriers in order to propel the concentrate through a syringe or sprayer, or for greater solubility and efficacy. It may also be desirable in some circumstances to include a viscosity control agent. Furthermore, while it is estimated that the shelf life of the improved medicine is two years, it may be necessary to add an appropriate preservative.

For preferred use, as a microbicide preventative against HIV, the medical solution (medicine) should be applied systemically, vaginally or rectally. The method of application of medicine can be by: syringing, spraying, dabbing, dropper, or other methods. The application or coating of the solution (medicine) should be maintained during coitus. Anionic soaps and anionic detergents, and especially protein content soaps can be contraindicated. Preferably, the area of application should be washed, cleaned and dried prior to application of the medicine. For treatment as an HIV antiviral, the medicine can be applied by syringing the dosage treatment into the rectum or vagina or by other methods.

Benzalkonium Chloride

A preferred surfactant is benzalkonium chloride. Benzalkonium chloride in aqueous solution is commercially available under the brand name and trade mark Zephiran® distributed by Sanofi Winthrop Pharmaceuticals (formerly Winthrop Labs). Benzalkonium chloride is a rapidly acting anti-infective surfactant with a moderately long duration of action. The surfactant is active against bacteria and some viruses, fungi and protozoa. Bacterial spores are considered to be resistant. Solutions of benzalkonium chloride are bacteriostatic or bacteriocidal according to concentration. The exact mechanism of bacterial action of benzalkonium chloride is unknown but is thought to be due to enzyme inactivation. Activity of benzalkonium chloride generally increases with increasing temperature and pH. Gram-positive bacteria are more susceptible to benzalkonium chloride than gram-negative bacteria.

Unfortunately, berizalkonium chloride is inactivated by soaps, anionic detergents, serum, and certain proteins. Benzalkonium chloride has fallen out of favor in many laboratories for the above reasons. When benzalkonium chloride was used alone and tested topically in vivo, it was ineffective for herpes simplex infectious outbreaks. When tested in vitro on HIV and HSV1 & 2 benzalkonium chloride demonstrated undesirable high levels of toxicity to the cells even at high dilutions, which is medically unacceptable. The chemical formula of benzalkonium chloride is shown below. Other types of benzalkonium chloride can be used.

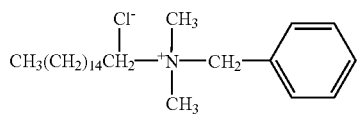

Benzalkonium Chloride

Phytochemicals

While raw, untreated, unprocessed, non-isolated *Echinacea* is generally undesirable to treat HIV and herpes intramurally, when, appropriately filtered, intramural administration may be feasible. Significantly, it appears that some, but not all, of the isolated constituents and botanical extracts of *Echinacea* and *Commiphora* (as previously described above) provide phytochemicals, antimicrobial isolates, botanical extracts and microbe inhibiters which have or exhibit antimicrobial activity that appear to be effective in treating HIV, herpes virus and other infectious diseases.

As previously stated, the phytochemical concentrate composition comprises the following isolated constituents, botanical extracts, microbial inhibitors, and antimicrobial isolates: polysaccharides, echinacen, echinaceine, echinacoside (caffeic acid ester), echinolone, echinadiol, enzymes, glucuronic acid, inuloid, pentadecadiene, polyacelylene compounds, arabinogalactan, rhamnose, PS I (a 4-0-methylglucoronoarabinoxylan, $M_r$ 35 kD) and PS II (an acid rhamnoarabinogalactan, $M_r$ 450 kD), cynarin (1,5-di-0-caffeoylquinic acid), acid (2,3-0-di-caffeoyltartaric acid) and derivatives, alklylamides, keto-alkynes and -alkenes; quinones; oils including: borneol, bornyle acetate; pentadeca-8(z)-en-2-one; germacrene D; caryophyllene; caryophylle epoxide; anthocyanins pyrrolizidine alkaloids; lipophilic amides; isobutylamides; polyacetylenes; myrrha gum resin; curzerenone (furahoeudesmane type); dihydro fuanodien-6-one; 2-methoxyfuranodiene (furanoelemene type); elamol; lyndestrene (furanogermacrane type); alkylamides, apigenin, arabinogalacta, ascorbic acid, behenic-acid-ethyl-acid, betaine, borneol, bornyl-acetate, caffeic-acid, 2-0-caffeoyl-3-(5-alpha carboxybeta) 3,4 dihydroxyphenly, 2-0-caffeoyl-3-0 cumaroyltaraic acid, 6-0-caffeoylechinacoside, 2-0-caffeoyl-3-0-feruloyltartaric acid, 2-0-caffeoyltartaric acid, calcium, carbonate, beta carotene, carophyllene, carophyllene-epoxide, chloride, chlorgenic acid, cichoric acid, cichoric-acid-methyl-ester, cobalt, cyanadin-3-0-(beta-d-glycopyranoside), cynadin-3-(6-0-malonyl beta-d-glycopyranoside), cynarin, deca (2e,4e,6e) trienoic acid-isobutylamide, des-rhamnosylverbascoside, 3,5-dicaffeoylquinic acid, 4-5-0 dicaffeoylquinic acid, 2,3-0-diferuloltartaric acid, do-deca-(2e,4e)-dienoic acid-isobutylamide, dodeca-2,4-dien-1-yl isovalerate, dodeca (2e,6z,8e,10e)-tetraenoic acid-isobutylamide, epishobunol, beta-farnesene, 2-0-feruloytartaric acid, germacrene, heptadeca-(8z,11z)-dien-2-one, heteroxylan, humulene 8-12, (e)-10-hydroxy-4,10-dimethyl 4,11-dodecadien-2-one, 13-hydroxyoctadeca-(9z, 11e, 15z)-trienoic-acid, inulin, iron, isochlorogenic acid, isorhamnetin-3-rutinoside, isotussilagine, kaempferol, kaempferol-3-glucoside, kaempferol-3-nutinoside, limonene, luteolin, luteolin-7-glucoside, magnesium, manganese, 2-methyltetradeca-5,12 diene, 2-methyltetradeca-6,12 dience, methyl-p-hydroxycinnamate, marcene, niacin, palmitic acid, pentadeca-(8z,11z)-dien-2-one, pentadeca-(8z,13z)-dien-11-lyn-2-one, pentadeca-8-en-2-one, pentadeca-(8z)-en 2 one, pentadeca-(8z)-en-11,13 dien-2-one, 1-pentadecene, penta-(1,8z)-diene, phosphorous, alpha pinene, beta pinene, polyacetylenes, pontica epoxide, potassium, protein, quercetagetin-7-glucoside, quercetin, quercetin-3-galactoside, quercetin-3-glucoside, quercetin-3-robinoside, quercetin-3-xyloside, quercetin-3-xylosylgalactoside, rhamnoarabinogalactan, riboflavin, rutin, rutoside, selenium, silicate, beta-sitosterol, sitosterol-3-beta o-glucoside, sodium, stigmasterol, sulfate, tartaric acid, tetradeca-(8z)-en-11,13 dien-2-one, thiamin, n-triacontanol, trideca-1-en-3,5,7,9,10-pentayne, tussilagine, vanallin, verbascoside sequiterpenes; acetic acid, alpha-amyrone, arabinose, alpha-bisabolene, gamma-bisabolene, cadinene, campesterol, cholesterol, cinnamaldehyde, commiferin, alpha-commiphoric acid, beta-commiphoric acid, gama-commiphoric acid, commiphorinic acid, m-cresol, cumic alcohol, curninaldehyde, dipentene, elemol, 3-epi-alpha-amyrin, eugenol, furanodiene, furanodienone, galactose, gum, heerabolene, alpha-heerabomyrrhol, beta-heerabomyrrhol, heeraboresene, limonene, 4-0-methyl-glucuronic acid, n-nonacesane, beta-sitosterol, xylose, caropylenes (carophylenes), lynderstyrene (indestyrene), caropylenes (carophylenes), myrrha gum resin, curzenone, dihydro frianodine-6-one, 2-methoxyfurandiene, and lynderstyrene (lindestyrene).

The chemical formula of some of the botanical extracts of *Echinacea* are shown below.

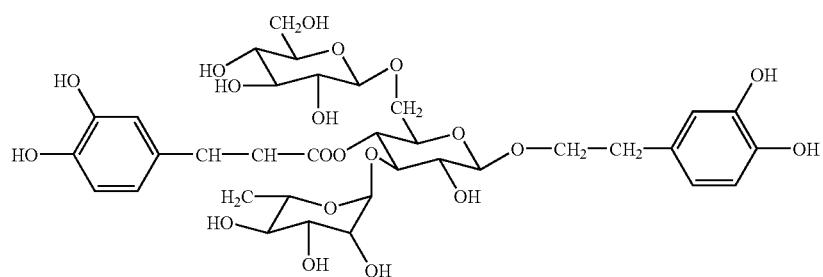

Echinacoside

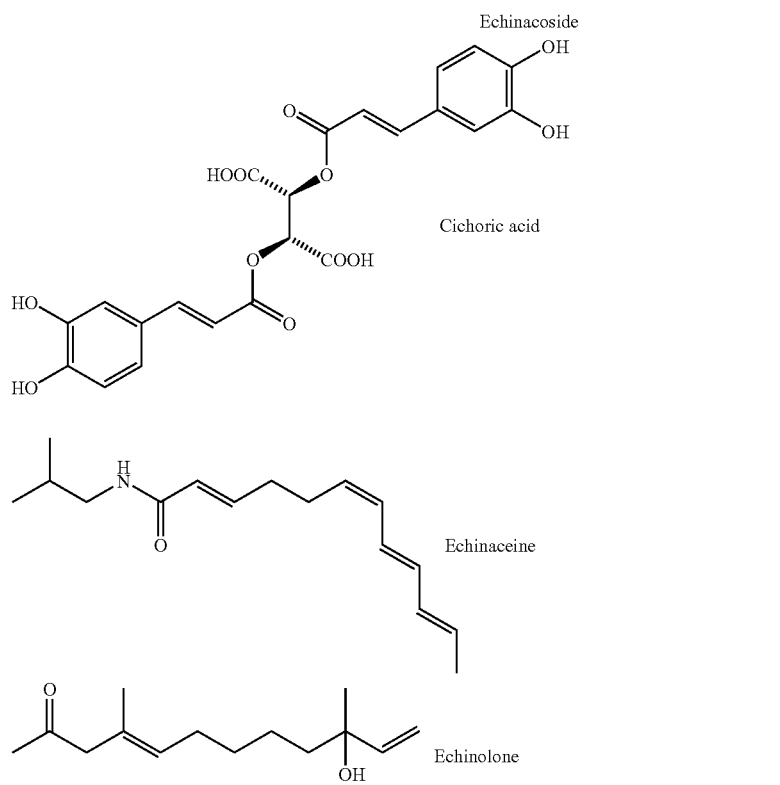

Cichoric acid

Echinaceine

Echinolone

The chemical formula of some of the botanical extracts of *Commiphoria myrrha* are shown below.

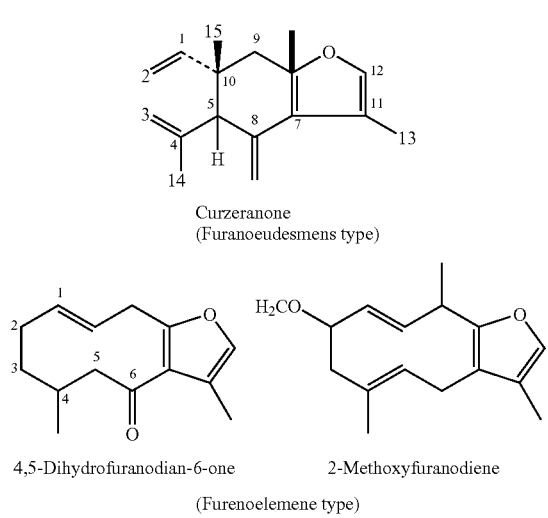

Curzeranone
(Furanoeudesmens type)

4,5-Dihydrofuranodian-6-one      2-Methoxyfuranodiene (Furenoelemene type)

-continued

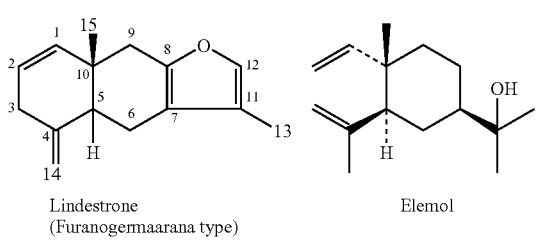

Lindestrone                Elemol
(Furanogermaarana type)

Myrrha is also sometimes referred to as: myrrh, mirre, myrrhis, gummi myrrha, myrrha vera, gum myrrh, *Commiphora* resin, gruggal gum, gruggal resin, *Heerabol* myrrh, myrrhe, *Manniliche* myrrhe, *Opopanax*, and *Hirabol* myrrh. Myrrha can comprise gum resin obtained from cuts made in the bark of trees of the genus *Commiphora myrrha*, i.e. the myrrh tree. Myrrha can also comprises balsamic juices from *Balsamodendron* myrrha, i.e., the Arabian myrtle, a buraceous tree. Myrrha can also be extracted from *Osmorhiza* or *Washingtonia*, which is also sometimes referred to a sweet cicely. The myrrh tree is a native in Erythrea, Abyssinia, Somalia, Yemen, Sudan, and elsewhere.

The myrrh-producing *Commiphora* species are shrubs or small trees with large, sharply pointed thorns on the stem. The unequal ternate leaves are alternate and the small flowers are arranged in terminal panicles. When damaged, the schizogenous resin ducts yield the drug myrrh.

Myrrha is an air-dried oleo-gum resin that exudes from the bark of *Commiphora* species. The material comprises irregular, rounded grains or lumps of varying sizes with holes and ranging in colour from dark brown and almost black to light or dark orange-brown; some parts may be yellow or colourless to pale yellow. The surface is mostly covered with a grey to yellowish grey powder; the fracture is conchoidal and yields thin, translucent fragments. Myrrha can have a sweet fragrance and a harsh and aromic order. Myrrha can have a bitter and aromatic taste. Myrrha can be acrid and can stick to the teeth on chewing.

*Commiphora molmol* and other *Commiphora* species, insofar as the chemical composition of their gum-resin, is comparable with that of myrrha DAB 10. There is considerable confusion in the literature regarding the sources of myrrh and the identity of the *Commiphora* species involved. Common (or hirabol) myrrh appears to derive from *Commiphora myrrha*. Somalian myrrh is said to come from *Commiphora molmol*. However, the systematic (taxonomic) relationship between *Commiphora myrrha* and *Commiphora molmol* is not clear. The source of *Abyssinian myrrh* is *Commiphora madagascariensis* or *Commiphora abyssinica*. *Opopanax*, which is also referred to as bisabol myrrh or perfumed bdellium is believed to originate from either *Commiphora erythraea* (Ehrenb) or *Opopanax*.

The composition of myrrha is very complex and only partially known from 40–60% of myrrha is soluble in ethanol and comprises a resin and an essential oil. Myrrha consists almost entirely of sesquiterpenes. The main components of sesquiterpenes are: furanosesquiterpenes of the germacrane elemane, eudesmane, and guaiane types. In addition, there are sesquiterpene hydrocarbons, e.g. β and δ-elemene, β-bourbonene, β-caryophyllene, humulene, and sesquiterpene alcohols, e.g. elemol. Presumably, some of the furanosesquiterpenes are characteristic of pharmaceutical myrrh. Myrrha curde gum or crude mucilage includes 20% proteins and 65% carbohydrates which are made up of galactose, 4-0-methylglucuronic acid, and arabinose. *Commophora myrrhaphyto* chemicals comprise: acetic acid, alpha-amyrone, arabinose, alpha-bisabolene, gamma-bisabolene, cadinene, campesterol, cholesterol, cinnamaldehyde, commiferin, alpha-commiphoric acid, beta-commiphoric acid, gama-commiphoric acid, commiphorinic acid, m-cresol, cumic alcohol, cuminaldehyde, dipentene, elemol, 3-epi-alpha-amyrin, eugenol, furanodiene, furanodienone, galactose, gum, heerabolene, alpha-heerabomyrrhol, beta-heerabomyrrhol, heeraboresene, limonene, 4-0-methyl-glucuronic acid, n-nonacesane, beta-sitosterol, xylose, caropylenes (carophylenes), myrrha gum resin, curzenone, dihydro fuanodien-6-one, 2-methoxyfurandiene, and lynderstyrene (lindestyrene).

The tincture of myrrha can have an anti-inflammatory effect. Macro and microscopically, myrrha can appear as a brownish yellow powder characterized by yellowish splinters or spherical grains of various sizes, along with fine granular material which swells in water. In chloral-hydrate mounts, there are only a few fragments of tissue from the plant source: reddish brown fragments of cork, individual and groups of polyhedral to oblong stone cells, partly with greatly thickened, pitted, and lignified walls and brownish contents; fragments of thin-walled parenchyma and sclerenchymatous fibres, and 10–25 μm irregular prismatic to polyhedral crystals of calcium oxalate.

Myrrha should be protected from light and moisture in well-closed containers. It is best with a desiccant, since the carbohydrate part of the drug readily absorbs water. Preferably, myrrha should not be stored in powdered form.

Folic Acid

The preferred nutrient is folic acid for best results. Folic acid, also referred to as folacin, pteroylglutamic acid, foldine, folaemin, foliamin, folicet, folipac, follettes, folsan, folvite, incafolic, millafol or cytofol, is a yellow, crystalline, water-soluble vitamin of the B complex group essential for cell growth and reproduction. Folic acid functions as a coenzyme with vitamins $B_{12}$ and vitamin C in the breakdown and utilization of proteins and in the formation of nucleic acids and heme in hemoglobin. Folic acid also increases the appetite and stimulates the production of hydrochloric acid in the digestive tract. Folic acid is stored in the liver and may be synthesized by the bacterial flora of the gastrointestinal tract. Deficiency of folic acid can result in poor growth, graying hair, glossitis, stomatitis, gastrointestinal lesions, and diarrhea, and it may lead to megaloblastic anemia. Deficiency is caused by inadequate dietary intake of the vitamin, malabsorption, or metabolic abnormalities. Need for folic acid is increased as in pregnancy, infancy, and stress. Folic acid is both heat and light labile, and considerable loss of the vitamin occurs when it has been stored for a long period. Folic acid is nontoxic and is effective in treating specific deficiency states. The chemical formula of folic acid is shown below.

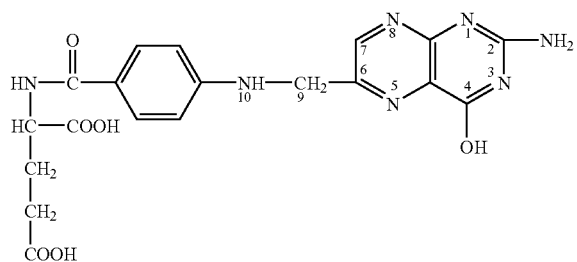

Folic acid (pteroylglutamic acid)

The structure of folic acid is presented below:

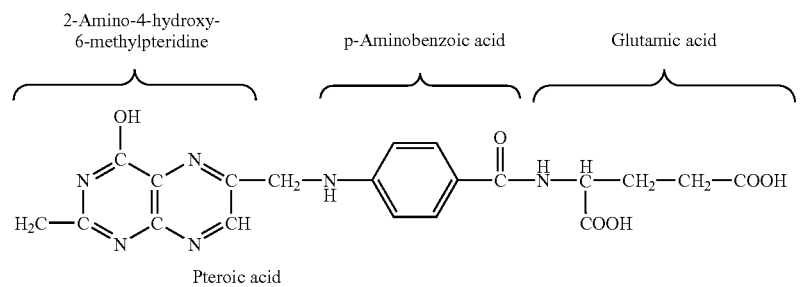

Pteroylglutamic Acid (Folic Acid)

The folic acid molecule contains glutamic acid, p-aminobenzoic acid, and a pterin; the combination of the pterin and p-aminobenzoic acid is termed pterocid acid. The structure shown is the pteroylglutamic acid of liver. The folic acid produced by bacteria contains three glutamic acid residues combined in γ-glutamyl linkage. Many animal tissues contain pteroylheptaglutamic acid, the glutamic acid residues again being in γ-glutamyl linkage. Synthetic pteroylpolyglutamic acids, in which the glutamic acid molecules are linked in a -glutamyl bonds, are active in bacterial growth assays; pteroyl-γ—glutamic acids are effective both in bacteria and in the treatment of macrocytic anemia in man. An enzyme in animal tissues hydrolyzes the naturally occurring pteroylpolglutamate compounds to pteroylmonglutamic acid and free glutamic acid.

Another structural formula of pteroylglutamic acid ($PteGlu_1$) is shown below.

Vitamin $B_{12}$ and folic acid are dietary essentials for man. A deficiency of either vitamin results in defective synthesis of DNA in any cell that attempts chromosomal replication and division. Since tissues with the greatest rate of cell turnover show the most dramatic changes, the hematopoietic system is especially sensitive to deficiencies of these vitamins. Clinically, the earliest sign of deficiency is a megaloblastic anemia, where the derangement in DNA synthesis results in a characteristic morphological abnormality of the precursor cells in the bone marrow. Abnormal macrocytic red blood cells are the product, and the patient becomes severely anemic.

Methylcobalarnin supports the methionine synthetase reaction, which is essential for normal metabolism of folate. Methyl groups contributed by methyltetrahydrofolate ($CH_3H_4PteGlu_1$) are used to form methylcobalamin, which then acts as a methyl group donor for the conversion of homocysteine to methionine. This folate-cobalamin interaction is pivotal for normal synthesis of purines and pyrim-

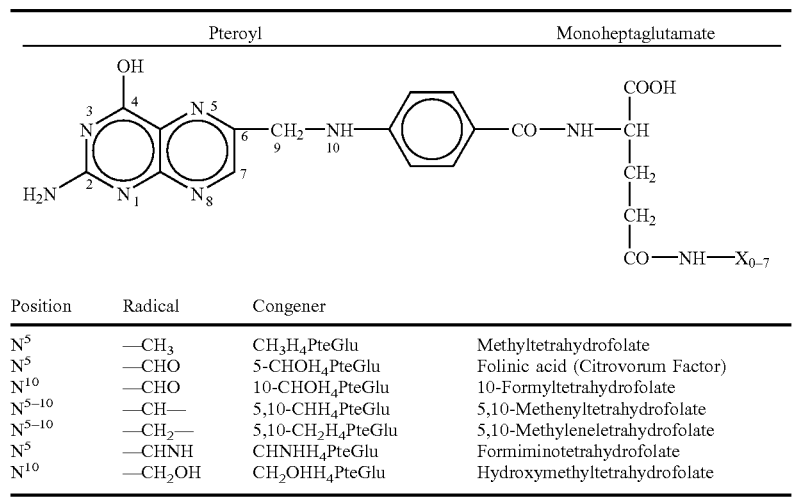

| Position | Radical | Congener | |
|---|---|---|---|
| $N^5$ | —$CH_3$ | $CH_3H_4PteGlu$ | Methyltetrahydrofolate |
| $N^5$ | —CHO | 5-$CHOH_4PteGlu$ | Folinic acid (Citrovorum Factor) |
| $N^{10}$ | —CHO | 10-$CHOH_4PteGlu$ | 10-Formyltetrahydrofolate |
| $N^{5-10}$ | —CH— | 5,10-$CHH_4PteGlu$ | 5,10-Methenyltetrahydrofolate |
| $N^{5-10}$ | —$CH_2$— | 5,10-$CH_2H_4PteGlu$ | 5,10-Methyleneletrahydrofolate |
| $N^5$ | —CHNH | $CHNHH_4PteGlu$ | Formiminotetrahydrofolate |
| $N^{10}$ | —$CH_2OH$ | $CH_2OHH_4PteGlu$ | Hydroxymethyltetrahydrofolate |

The structures and nomenclature of pteroylglutamic acid (folic acid).

Major portions of the folic acid molecule include a pteridine ring linked by a methylene bridge to paraminobenzoic acid, which is joined by an amide linkage to glutamic acid. While pteroylglutamic acid is the common pharmaceutical form of folic acid, it is neither the principal folate congener in food nor the active coenzyme for intracellular metabolism. Following absorption, $PteGlu_1$ is rapidly reduced at the 5, 6, 7, and 8 positions to tetrahydrofolic acid ($H_4PteGlu_1$), which then acts as an acceptor of a number of one-carbon units. These are attached at either the 5 or the 10 position of the pteridine ring or bridge these atoms to form a new five-membered ring.

idines and, therefore, of DNA. The methionine synthetase reaction is largely responsible for the control of the recycling of folate cofactors; the maintenance of intracellular concentrations of folylpolyglutamates; and, through the synthesis of methionine and its product, S-adenosylmethionine, the maintenance of a number of methyylation reaction. Since methyltetrahydrofolate is the principal folate congener supplied to cells, the transfer of the methyl group to cobalamin is essential for the adequate supply of tetrahydrofolate ($H_4PteGlu_1$), the substrate for a number of metabolic steps. Tetrahydrofolate is a precursor for the formation of intracellular folylpolyglutamates; it also acts as the acceptor of a one-carbon unit in the conversion of serine to glycine, with the resultant formulation of 5,10 methylenetetrahydrofolate (5,10-$CH_2H_4PteGlu$). The latter derivative donates the methylene group to deoxyuridylate for the synthesis of thymidylate-an extremely important reaction in DNA synthesis. In the process, the 5,10-CH₂H₄PteG1 is converted to dihydrofolate (H₂PteGlu). The cycle is then completed by the reduction of the H₂PteGlu to H₄PteGlu by dihydrofolate reductase, the step that is blocked by folate antagonists such as methotrexate. Other pathways also lead to the synthesis of 5,10 methylenetetrahydrofolate.

TABLE A

Biosynthesis of Folic Acid

The biosynthesis of folic acid is shown below. The symbol ppp represents triphosphate.

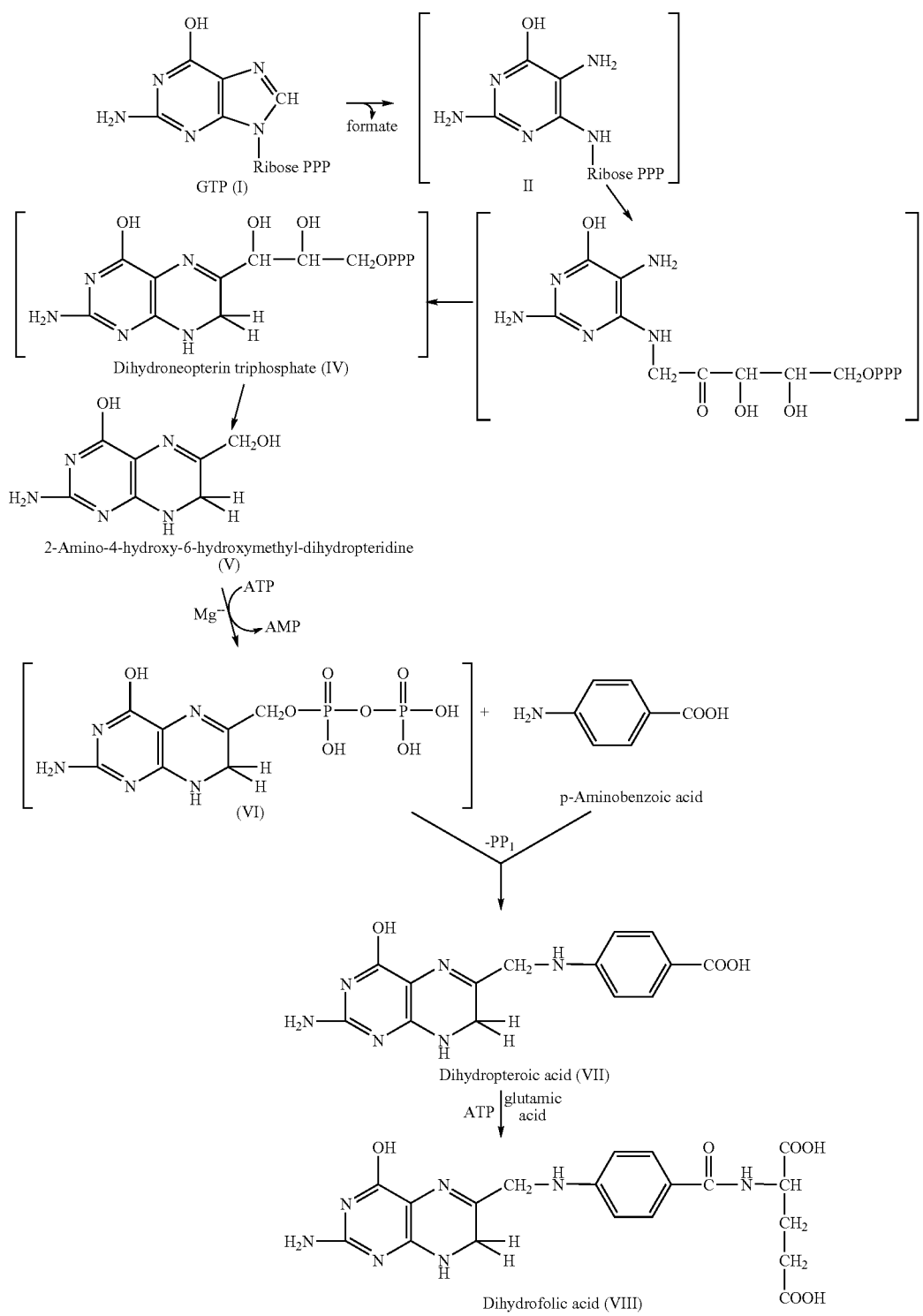

Folate can be transported to tissues as $CH_3H_4PteG_1$. The liver actively reduces and methylates $PteGlu_1$ (and $H_2$ or $H_4PteGlu_1$) and then transports the $CH_3H_4PteGlu_1$ into bile for reabsorption by the gut and subsequent delivery to tissues, $CH_3H_4PteGlu$ acts as a methyl donor for the formation of methylcobalamin and as a source of $H_4PteGlu$ and other folate congeners, as described previously. Folate is stored within cells as polyglutamates.

Surfactants

While benzalkonium chloride is the preferred surfactant for best results, in some circumstances it may be desirable to use other quanternay ammonium surfactants or other surfactants.

The quaternary ammonium compound can be dicocodimonium chloride, which is also known as dicoco alkyldimethyl, chlorides or dicoco dimethyl ammonium chloride or Dl-C8–18-alkyldimethyl, chlorides. This can be used in combination with isopropanol, such as 20–30% isopropanol. The preferred source of quaternary ammonium compound comprises: 70–80% quaternary ammonium compound and less than 0.03% methyl chloride, has a specific gravity of about 0.87 at 115 degrees F., a vapor pressure of 33 mm/Hg at 68 degrees F., an initial boiling point of 180 degrees F. at 760 mm/Hg, and a volatility of 20–30%, and is produced under the brand name CarSpray 300 by Witco Corporation, Dublin, Ohio, USA. The quaternary compound can provide disinfecting qualities and serves as a fungicide to teat fungus and yeast infections.

Other quaternary ammonium compounds may be useful, such as produced under the brand name Jet Quat 2C-75 by Jetco Chemicals, Inc. of Corsicana, Tex., USA, or produced under the brand names Carspray 400 and Carnauba Spray 200 by Witco Corporation, Dublin, Ohio, USA, or containing 9% denatured ethyl alcohol such as sold under the brand name BTC 2125M by Stephan Company, Northfield, Ill., USA, or the following MAQUAT products comprising n-alkyl dimethyl benzyl ammonium chloride produced by Mason Chemical Company, Arlington Heights, Ill., USA. LC-12S (67% C12, 25% C14, 7% C16, 1% C18), MC 1416 (5% C12, 60% C14,30% C16, 5% C18), MC1412 (40% C12, 50% C14, 10% C16), SC-18 stearyl paste or flake (5% C16, 95% Cl8), TC-76 or MQ-2525 (5% C12, 60% C14, 30% C16, and 5% C18) and MC6025–50% (25% C12, 60% C14 and 15% C16). Jet Quat 2C-75 comprises: 50–75% dicoco dimethyl quaternary ammonium chloride, 20–50% isopropyl alcohol, has a specific gravity of 0.88 and a boiling point of 180 degrees F. CarSpray 400 comprises: 55–65% quaternary ammonium compounds, 20–30% amines, C14–18 & C16–18 unsaturated, alkyl, ethoxylated, 10–20% isopropanol, and less than 0.03% methyl chloride, and has a specific gravity of approximate 0.88 at 75 degrees, F., a vapor pressure of 33 mm/Hg at 68 degrees F., an initial boiling point of 180 degrees F. at 760 mm/Hg, and a volatility of 10–20%. Carnauba Spray 200 comprises: 50–60% quaternary ammonium compounds, 10–20% isopropanol, 15–25% water, 1–10% alkoylated carnauba wax, and less than 0.03% methyl chloride, and has a specific gravity of about 0.90 at 80 degrees F., a vapor pressure of 33 mm/Hg at 68 degrees F., an initial boiling point of 180 degrees F. at 760 mm/Hg, and a volatility of 20–40%.

Nonionic surfactants are surface-active compounds which do not ionize in water solution. Often times these possess hydrophilic characteristics by virtue of the presence therein of an oxygenated chain (e.g., a poly-oxyethylene chain), the lyophilic portion of the molecule being derived from fatty acids, phenols, alcohols, amides or amines. Exemplary compounds are the poly-(ethylene oxide) condensates of alkyl phenols, e.g. the condensation product formed from one mole of nonyl phenol and ten moles of ethylene oxide, and the condensation products of aliphatic alcohols and ethylene oxide, e.g. the condensation product formed from 1 mole of tridecanol and 12 moles of ethylene oxide.

The nonionic surfactants can comprise phenol ethoxylates comprising a condensate product of ethylene oxide and an alkyl phenol or an aliphatic alcohol. The nonionic surfactants preferably comprise nonophenol ethoxylate such as T-DET, and/or octaphenol ethoxylate. The nonionic surfactants are reaction products of ethylene oxide and nonolphenol and/or octalphenol. The ratio of the phenol to the ethylene oxide can range from 2:20 to 4:16 and preferably is about 8:12.

Nonionic synthetic surfactants can comprise nonionic detergents. Nonionic synthetic surfactants can also be formed by condensing ethylene oxide with a hydrophobic base formed by the condensation of propylene oxide with propylene glycol. The hydrophobic portion of the molecule which, of course, exhibits water insolubility has a molecular weight of from about 1200 to 2500. The addition of polyoxyethylene radicals to this hydrophobic portion tends to increase the water solubility of the molecule as a whole and the liquid character of the product can be retained up to the point where polyoxyethylene content is about 50% of the total weight of the condensation product. Other nonionic synthetic surfactants can include: the polyethylene oxide condensates of alkylphenols, e.g. the condensation products of alkylphenols or dialkylphenols wherein the alkyl group contains from about 6 to 12 carbon atoms in either a straight chain or branched chain configuration, with ethylene oxide. The ethylene oxide can be present in amounts equal to 8 to 25 moles of ethylene oxide per mole of alkylphenol. The alkyl substituent in such compounds can be derived from polymerized propylene, diisobutylene, n-octene, or n-nonene.

Nonionic surfactants can also be produced from the condensation of ethylene oxide with the reaction product of propylene oxide and ethylenediamine, e.g. compounds containing from about 40% to about 80% polyoxyethylene by weight and having a molecular weight of from about 5,000 to about 11,000 resulting from the reaction of ethylene oxide groups with a hydrophobic base comprising the reaction product of ethylenediamine and excess propylene oxide; the base having a molecular weight on the order of 2,500 to 3,000.

Other nonionic surfactants include the condensation product of aliphatic alcohols having from 8 to 18 carbon atoms, in either straight chain or branched chain configuration, with ethylene oxide, e.g. a coconut alcohol ethylene oxide condensation having from 10 to 30 moles of ethylene oxide per mole of coconut alcohol, and the coconut alcohol fraction having from 10 to 14 carbon atoms.

Further nonionic surfactants include long chain tertiary amine oxides corresponding to the following general formula:

$$R_1R_3R_2N \rightarrow O$$

wherein R1 is an alkyl radical of from about 8 to 18 carbon atoms, and $R_2$ and $R_3$ are each methyl or ethyl radicals. The arrow in the formula is a conventional representation of a semi-polar bond. Examples of amine oxides suitable for use include: dimethyldodecylamine oxide, dimethyloctylamine oxide, dimethyldecylamine oxide, dimethyltetradecylamine oxide, and dimethylhexadecylamine oxide.

Other nonionic surfactants can include: long chain tertiary phosphine oxides corresponding to the following general formula

wherein R is an alkyl, alkenyl or monohydroxyalkyl radical ranging from 10 to 18 carbon atoms in chain length and R' and R" are each alkyl or monohydroxyalkyl groups containing from 1 to 3 carbon atoms. The arrow in the formula is a conventional representation of a semi-polar bond. Examples of suitable phosphine oxides are: dimethyldodecylphosphine oxide, dimethyltetradecylphosphine oxide, ethylmethyltetradecylphosphine oxide, cetyldimethylphosphine oxide, dimethylstearylphosphine oxide, cetylethylpropylphosphine oxide, diethyldodecylphosphine oxide, diethyltetradecylphosphine oxide, dipropyldodecylphosphine oxide, bis-(2-hydroxymethyl)dodecylphosphine oxide, bis-(2-hydroxyethyl)dodecylphosphine oxide, (2-hydroxy propyl)methyltetradecylphosphine oxide, dimethyloleylphosphine oxide, and dimethyl-(2-hydroxydodecyl) phosphine oxide.

In some circumstances it may be useful to use other surfactants such as: another cationic surfactant, an ampholytic surfactant or a zwitterionic surfactant.

The cationic surfactants can include cationic detergents. The cationic surfactants comprise compounds which ionize in an aqueous medium to give cations containing the lyophilic group. Typical of these compounds are the quaternary ammonium salts which contain an alkyl group of about 12 to about 18 carbon atoms, such as lauryl benzyl dimethyl ammonium chloride.

Ampholytic surfactants are compounds having both anionic and cationic groups in the same molecule. Exemplary of such compounds are derivatives of aliphatic amines which contain a long chain of about 8 to about 18 carbon atoms and an anionic water solubilizing group, e.g., carboxysulfo, sulfo or sulfato. Examples of ampholytic detergents are: sodium-3-dodecylaminopropane sulfonate, sodium-N-methyl taurate, and related substances such as higher alkyl disubstituted amino acids, betaines, thetines, sulfated long chain olefinic amines, and sulfated imidazoline derivatives.

Zwitterionic surfactants can include synthetic detergents. Zwitterionic surfactants are generally derivatives of aliphatic quaternary ammonium compounds in which the aliphatic radical can be a straight chain or branched and wherein one of the aliphatic substituents contains from about 8 to 18 carbon atoms and one contains an anionic water solubilizing group, e.g., carboxy, sulfo, or sulfato. Examples of compounds falling within this definition are: 3-(N,N-dimethyl-N-hexadecyl ammonio)-propane-1-sulfonate and 3-(N,N-dimethyl-N-hexadecyl ammonio)-2-hydroxy propane-1-sulfonate.

Clinical Pharmacology

When the *Echinacea* and *Commiphora* phytochemicals (antimicrobial isolates, botanical extracts and microbe inhibitors) were mixed, combined and applied with: a surfactant, preferably benzalkonium chloride; a nutrient carrier, preferably folic acid; and a sterile aqueous carrier; the results were unexpected and surprisingly good in resolving (treating) HIV, and other infectious diseases and the effectiveness of the medicine (microbicide) dramatically increased. Significantly, when tested in vitro, the unique compound demonstrated unexpectedly and surprisingly good antiviral activity against HIV including inhibition of the attachment of HIV to target cells. When the synergistic medicine was tested topically in vivo, herpes simplex infections were immediately arrested. When the synergistic medicine was tested in vitro, the benzalkonium chloride surfactant was substantially less toxic and within a safe level and there was a higher level of inhibitory activity against HIV and HSV 1 & 2. The synergism interaction and mixing of the *Echinacea* and *Commiphora* phytochemicals, folic acid, and surfactant were demonstrated and observed by viewing the rapid solubility of the components when mixed and the slight adhesive quality created by the properties in solution. Furthermore, the chemical properties of the *Echinacea* and *Commiphora* phytochemicals, surfactant nutrient carrier (nutrient), and aqueous carrier enhanced stabilization and increased reactivity which is useful in treating infectious diseases.

The medicine can be used in varying dilutions on: oral and nasal mucosa; vaginal tissue; labial tissue; anal and peri-anal tissue; penile tissue; cutaneous tissue; open subcutaneous tissue; and in higher dilutions on ocular infections and preferably rectal or vaginal administration. By varying the concentrations, the medicine may possibly be administered parenterally. The medicine may be contraindicated in vaginal or anal passages; in pack dressing; in the ear canal; occlusive dressings; casts or ingestion and such use may produce irritation or chemical burns. It may not be advisable to use the medicine to treat anaerobic fungal infections, since some fungi may be resistant.

EXAMPLES 1–7

In vivo Testing

In an initial, topical application, in-vivo study that was undertaken to evaluate the effects of the medical treatment and medicine of the present invention upon seven human test subjects who had been tested positive for HSV 1 or 2. The subjects were treated topically with the medicine comprising benzalkonium chloride surfactant in an aqueous solution (at a ratio of 1:750) in combination with the herbaceous botanical *Echinacea purpurea* in powdered form containing the previously listed phytochemicals. Application of the composition was made by a two-step procedure by first wetting the affected area or vesicle with the benzalkonium chloride surfactant in an aqueous solution by spraying, dabbing, or using a dropper; then applying a coating of the powdered phytochemicals over the wetted area by either swab or manually sprinkling the powder onto the infected area. An important aspect in this treatment was maintaining complete coverage of the affected area for the duration of the outbreak. Therefore, the area of outbreak was kept covered with the medical composition by reapplying as needed.

Of the seven subjects, six were female, and one was male. At the beginning of this study, the age of the male was 38, the female subjects were ages 8, 27, 30, 32, 38, and 39. There were twelve infectious outbreaks over approximately six weeks. Nine of the outbreaks were HSV 2, genital herpes, and three were HSV1, cold sores. The 8 year old and the 27 year old females exhibited the HSV 1 (cold sores). The 30 year old, 38 year old and the 39 year old females exhibited the HSV 2 (genital herpes). The 38 year old also had a HSV 1 cold sore. The male exhibited HSV 2 (genital herpes). All subjects tested had a well established history of the disease and could identify the standard course of their disease. To obtain objective data, none of the test subjects knew anything about the test treatment or any action of the medicine. On repeat tests, the subjects were told that there may be placebos mixed in the samples of formula.

In seven cases, the antimicrobial compound (medicine) was applied directly on tissue at the prodrome stage. In five cases, the antimicrobial compound was applied directly on erupted vesicles. The antimicrobial compound was reapplied as necessary to maintain coverage.

Observations: With each application of the medicine, each individual (test subject) reported a tingling sensation for a few seconds. They also reported that there was a substantial degree of adherence of the medicine (antimicrobial) compound to the vesicle(s) or affected area. The adherence of the composition to the epithelial tissue remained to a degree even after showering or water rinsing the area.

Results: The results of the testing of the 7 subjects with the medical treatment and medicine were unexpectedly surprisingly good and very consistent. In each case, the subject happily reported that once the composition (medicine) was applied to the affected area, the pain completely stopped within 10 to 20 minutes when nothing in the past had ever eased pain before. In the seven cases, where the compound (medicine) was applied at the prodrome stage, the subjects reported that the pain stopped, all symptoms that would have previously escalated to full outbreak ceased and the outbreak never again occurred. All external symptoms and physical manifestations of herpes disappeared within a few hours after the medicine was applied. In the five cases, where the compound (medicine) was applied to erupted vesicles, the subjects reported that the pain stopped in minutes and the burning, itching and irritation resolved in two to four hours and the vesicles dried up and were gone in twenty-one hours. In all cases, the other more extreme, debilitating symptoms of: fever, malaise, inguinal swelling, weeping sores and painful urination stopped, once the medicine was applied.

In follow-up, where subjects had been given a supply of the composition (medicine) to test on future outbreaks, it was reported that if the initial signs of an outbreak exhibited, signaling the prodrome stage of an outbreak, the compound (medicine) was immediately applied by the subjects as per instructions and the outbreak was fully arrested and resolved. Significantly, it was also reported by subjects who were accustomed to experiencing several outbreaks annually, that they had remarkably longer latency periods. In a three year follow-up with one individual who had reported severe outbreaks monthly for four years prior to use of this medicine, she now reports that she has not had an outbreak in over a year since using this medicine.

Additional Observations: One human male subject reported that after the initial application during the prodrome phase of an outbreak, he showered and forgot to reapply the composition (medicine) for a period of approximately 30 hours. Consequently, several vesicles erupted and began to coalesce. The subject proceeded to reapply the composition (medicine) and thereafter kept the area well coated with the composition. Subsequently, the outbreak resolved in 21 hours in the same manner as described with the other human subjects.

Another observation indicated that the composition (medicine) may be weakened or less effective in the presence of certain proteins or soaps. One human female subject, may have been overly zealous in cleansing the affected area prior to application of the composition (medicine). This occurred during a third outbreak after having success with the composition (medicine) on the two prior outbreaks. In this instance, when the composition (medicine) was applied, there was no familiar tingling sensation and no relief from symptoms. Approximately 24 hours elapsed before she sought any advice and the outbreak had escalated to the full vesicular eruption stage with all the foregoing symptoms of the disease. She was instructed to thoroughly rinse any soap residue from the area, dry the area and reapply the composition (medicine). After following the instructions, she reported that the outbreak has been fully resolved, as it had in the two prior outbreaks, by applying the medical composition.

EXAMPLES 8–13

Dermatological and Veterinary Testing

Animal testing to determine any possible dermatological allergic reaction induced by the medical composition (medicine) was undertaken. Six animal subjects were used. The animals included 3 female rabbits (ages unknown); 2 dogs (1 female 2 year old, and 1 male 9 year old); one, 3 year old neutered male cat. In these animal tests, the above composition (medicine) was applied, in the previously stated method, to the inside of the outer ear of each animal. In all instances, the area being treated was kept coated with the compound for twenty-four hours, matching the time human subjects had used. The testing performed on the six animal subjects indicated that there were no signs of dermatological irritation or allergic reaction.

EXAMPLE 14

The above medical compound containing viral inhibitors was also tested on a papilloma virus caused wart on the muzzle of a two year old gelded thoroughbred horse. Papilloma virus warts are difficult to treat. The wart measured 25 mm in diameter. The antimicrobial compound (medicine) was applied twice daily. The wart was then measured at each application.

Results: Quite unexpectedly, the wart decreased dramatically in size by approximately 3 mm per day while the medicine was applied to the wart and on the fifth day fell off completely. It was observed that, at first the surface layers of the wart began to degrade, exposing large erythematous papules. Then interestingly, the warts did not just diminish in size by flaking or peeling, they diminished at the point of attachment on the subject's epidermis and fell off still somewhat intact with no sequela scarring.

In an ongoing, long term in vivo study of this invention, which began with the first seven subjects in April of 1989 and has now spanned 7 years, approximately 100 infectious outbreaks have been treated with the medicine in different concentrations, as described previously. In all cases the surprisingly good results were the same: 1. Pain disappears in minutes; 2. No outbreak occurs when the composition is applied at the prodrome stage; 3. The outbreak resolves in twenty-one hours when applied at the vesicular stage.

In vitro Testing

Laboratory testing was undertaken at the University Of Chicago, Clinical Microbiology Laboratories to determine inhibitory activity in vit-o of the medical treatment and composition (medicine). The laboratory testing was conducted by the Associate Director, PhD, and Associate Professor of Pathology. The in vitro testing of the medical composition, referred to as the "Drug" below, yielded surprisingly good results. It was determined that the medical treatment and composition had unexpectedly, surprising excellent inhibitory activity on HSV 1 and HSV 2. It was stated by the pathologist, that he had tested "hundreds" of other compounds and had never seen anything as good as what this compound did.

The following are the tests of the medicine that were conducted and results that were obtained at The University of Chicago. For ease of interpreting some of the scientific data and test results, the following definitions apply:

"MEM" pertains to Minimal Essential Medium. This is the culture medium used in laboratories for growing the cells upon which tests were run.

"Fibroblast" is a mesenchyme human cell (a cell found in connective tissue, blood, bone, lymphatics, and cartilage).

"$IC_{50}$" pertains to the Inhibitory Concentrate. For this testing a 50% endpoint was selected, as is typical. The number following indicates the greatest dilution below 50%. Therefore it is the definition of the endpoint.

If an area under a dilution is left blank, it indicates that there may have been toxicity at that dilution, the test may not have been worth reading, or no interpretable data is available.

If an area under dilution is marked with a hyphen (-), it indicates that there are no plaques and there is a successful inhibition of herpes (HSV).

EXAMPLES 15–17

In these in vitro tests, the following drugs (medicine) was used:

Drug # 1.=Benzalkonium chloride surfactant in an aqueous solution at a ratio of 1:750. The surfactant in the aqueous solution was filtered before use and diluted in an equal volume of 2×MEM to give a 1:1500 dilution in 1×MEM.

Drug # 2=Echinacea powder (photochemicals) in an aqueous solution. This preparation was extracted by warm infusion in sterile water. The extracted phytochemicals was centrifiged and filtered before use. The filtered phytochemicals were diluted in an equal volume of 2×MEM to give the undiluted preparation in 1×MEM.

Drug # 3=Echinacea powder (phytochemicals) were extracted and combined with benzalkonium chloride surfactant by a cold infusion process. The combined preparation was centrifuged and filtered before use and diluted in an equal volume of 2×MEM to give the undiluted preparation in 1×MEM.

1. Three 24-compartment plates were inoculated with fibroblasts. Three different extractions (for comparison) in five concentrations of the composition were used to screen for antiviral activity in concentrations of: undiluted, 1:2, 1:4, 1:8, and 1:16 in 1×MEM. There were four control compartments on each plate containing MEM without drug.

2. The growth media was removed from the compartments and 200 ul of HSV-1 was added to each compartment of the upper half of each plate. HSV-1 was diluted 1:5000 (2.0 ul of stock HSV-1 in 10 mL of MEM). The virus titer was $3\times10^6$ per mL. Also, 200 ul of HSV-2 was added to each compartment of the lower half of each plate. HSV-2 was diluted 1:2,000 (5.0 ul of stock HSV-2 in 10 mL of MEM). The virus titer was $6\times10^5$ per mL.

3. The plates were incubated at 37° C. for two hours.

4. The inoculum was removed and one mL of the MEM containing Drugs #1–3 were added to the four compartments. The concentration of the drug compared to the MEM is indicated below.

TABLE 1

| Concentration | Undiluted | 1:2 | 1:4 | 1:8 | 1:16 |
|---|---|---|---|---|---|
| Drug (ul) | 4000 | 2000 | 1000 | 500 | 250 |
| MEM (ul) | — | 2000 | 3000 | 3500 | 3750 |

5. Results: HSV-1, liquid overlay, Drug added immediately after virus absorption.

Plate 1, Drug #1 contaminated with bacteria! No growth, maybe debris.

Plate 2, Drug #2 contaminated with bacteria! No growth, maybe debris.

Plate 3) Drug #3 The results are indicated in Tables 2 and 3 below.

TABLE 2

Drug #3 HSV 1 Test Results

| Concentration | undiluted | 1:2 | 1:4 | 1:8 | 1:16 | |
|---|---|---|---|---|---|---|
| plaques | 54 | toxic | toxic | — | 6* | 12** |
| plaques | 42 | toxic | toxic | — | 4* | 16** |
| Average | 48 | | | | 5 | 14 | $IC_{50} > 1:16$ |

TABLE 3

Drug #3 HSV 2 Test Results

| Concentration | undiluted | 1:2 | 1:4 | 1:8 | 1:16 | |
|---|---|---|---|---|---|---|
| plaques | 46 | toxic | toxic | — | 22* | 32** |
| plaques | 49 | toxic | toxic | — | 21* | 28** |
| Average | 48 | | | | 22 | 30 | $IC_{50} = 1:8$ |

*slight toxicity.
**very small plaques

Comments: Testing with the medicine (Drug #3) provided excellent results. The cells look fine with no contamination. At the lower dilutions, the preparation may be toxic to some of the cells. This preparation was unexpectedly successful in its inhibitory activity.

EXAMPLES 18–20

Three 24-compartment plates were inoculated with fibroblasts and the following drugs.

Test Drug #1A=Benzalkonium chloride surfactant in an aqueous solution. The benzalkonium chloride surfactant was prepared by making a 1:375 dilution in water (32 ul in 12.0 mL of sterile water). This was filtered before use. This was diluted in an equal volume of 2×MEM to give 1:750 dilution in 1×MEM. The dilution was done to maintain the ratio.

Test Drug #2A=*Echinacea purpurea* powder (phytochemicals) in an aqueous solution. This preparation was a 50 mg/mL solution (300 mg in 6.0 mL of water) of *Echinacea purpurea* powder in sterile water. The mixture was vortexed and refrigerated for four hours. The Echinacea powder preparation was centrifuged at 3500 rpm for 15 minutes at 10° C. and filtered before use and then diluted in an equal volume of 2×MEM to give the undiluted preparation in 1×MEM.

Test Drug #3A=*Echinacea purpurea* powder (phytochemicals) dissolved in benzalkonium chloride surfactant. This preparation was a 50 mg/mL solution (300 mg in 6.0 mL of benzalkonium chloride, 1:375). The mixture was vortexed and refrigerated for four hours. The phytochemical and surfactant mixture was centrifuged at 3500 rpm for 15 minutes at 10° C. and filtered before use, and then diluted in an equal volume of 2×MEM to give the undiluted preparation in 1×MEM.

1. Three plates were used to screen the three drug preparations. The concentrations needed to screen for antiviral activity were 1:2, 1:4, 1:8, and 1:16 in 1×MEM. There were four control compartments on each plate containing MEM without drug.

2. The growth media was removed from the compartments and 200 ul of HSV-1 was added to each compartment of the upper half of each plate. HSV-1 was diluted 1:5000 (2.0 ul of stock HSV-1 in 10 mL of MEM). The virus titer was $3 \times 10^6$ per mL.

3. The plates were incubated at 37° C. for four hours.

4. The inoculum was removed and one mL of the MEM containing drugs #1A-3A were added to the four compartments.

TABLE 4

| Concentration | Undiluted | 1:2 | 1:4 | 1:8 | 1:16 |
|---|---|---|---|---|---|
| Drug (ul) | 4000 | 2000 | 1000 | 500 | 250 |
| MEM (ul) | — | 2000 | 3000 | 3500 | 3750 |

5. Results: HSV-1, liquid overlay, composition added immediately after virus absorption.

TABLE 5

Drug #1A - HSV 1 Test Results

| Concentration | 1:2 | 1:4 | 1:8 | 1:16 | 1:32 |
|---|---|---|---|---|---|
| plaques | 70 | toxic | toxic | toxic | toxic | toxic |
| plaques | 68 | | | | |
| plaques | 58 | | | | |
| plaques | 74 | | | | |
| Average | 70 | | | $IC_{50}$ | |

Comments: These compartments have a fine precipitate over the cells. Benzalkonium chloride probably precipitates with the protein in the medium.

TABLE 6

Drug #2A - HSV 1 Test Results

| Concentration | 1:2 | 1:4 | 1:8 | 1:16 | 1:32 |
|---|---|---|---|---|---|
| plaques | 72 | — | — | — | 9* | 12* |
| plaques | 74 | — | — | — | 7 | 8 |
| plaques | 79 | — | — | — | 4 | 12 |
| plaques | 71 | — | — | — | 7 | 11 |
| Average | 70 | | | $IC_{50} > 1:32$ | | |

Comments: Although there were some plaques, they were very small.

TABLE 7

Drug #3A - HSV 1 Test Results

| Concentration | 1:2 | 1:4 | 1:8 | 1:16 | 1:32 |
|---|---|---|---|---|---|
| plaques | 72 | toxic | toxic | toxic | toxic | —* |
| plaques | 68 | | | | — |
| plaques | 67 | | | | — |
| plaques | 70 | | | | — |
| Average | 70 | | | $IC_{50} > 1:32$ | |

Comments: Although there was some toxicity, this drug was very successful in inhibiting the virus, there did not appear to be any plaques.

EXAMPLES 21–24

Four 24-compartment plates were inoculated with fibroblasts.

Test Drug #1B=Benzalkonium chloride surfactant in an aqueous diluent. The benzalkonium chloride was prepared by making a 1:1000 dilution in water (10 ul in 10.0 mL of sterile water). This was filtered before use and diluted in an equal volume of 2×MEM to give 1:2000 dilution in 1×MEM.(500 ul drug plus 500 ul of 2×MEM).

Test Drug #2B=*Echinacea purpurea* powder (phytochemicals) in an aqueous solution. This preparation was a 50 mg/mL solution (250 mg in 5.0 mL of water) of *Echinacea purpurea* powder in sterile water. The mixture was vortexed and refrigerated for four hours. This *Echinacea* powdered preparation was centrifuged at 3500 rpm for 15 minutes at 10° C. and filtered before use, and diluted in an equal volume of 2× MEM to give the undiluted preparation in 1×MEM.(500 ul drug plus 500 ul of 2×MEM).

Test Drug #3B=*Echinacea purpurea* powder (phytochemicals) dissolved in benzalkonium chloride surfactant. This preparation was a 50 mg/mL solution (250 mg in 5.0 mL of benzalkonium chloride, 1:1000). The mixture was vortexed and refrigerated for four hours. The *Echinacea* phytochemicals and surfactants were centrifuged at 3500 rpm for 15 minutes at 10° C. and filtered before use, and then diluted in an equal volume of 2×MEM to give the preparation in 1×MEM (500 ul drug plus 500 ul of 2×MEM).

Test Drug #4B=*Echinacea purpurea* powder (phytochemicals) in an aqueous solution (diluent) and then mixed with benzalkonium chloride surfactant at a ratio of 1:1000. This preparation was a 50 mg/mL solution (250 mg in 5.0 mL in 5.0 mL of water) of *Echinacea purpurea* powder in sterile water. The mixture was vortexed and refrigerated for four hours. The aqueous phytochemicals were centrifuged at 3500 rpm for 15 minutes at 10° C. and filtered before use. This preparation was diluted in an equal volume of benzalkonium chloride at a ratio of 1:1000, to get the *Echinacea*-benzalkonium chloride mixture. This mixture was diluted with equal volume of 2×MEM to give the 1:4 preparation in 1×EM (500 ul drug #1 and 250 ul drug #2 plus 500 ul of 2×MEM).

1. Four plates were used to screen the four drug preparations. The concentrations needed to screen for antiviral activity were 1:20, 1:40, 1:80, and 1:160 and 1:320 in 1×MEM. There were four control compartments on each plate containing MEM without drug.

2. The growth media was removed from the compartments and 200 ul of HSV-1 was added to each compartment of the upper two rows of each plate. HSV-1 was diluted 1:5000(2.0 ul of stock HSV-1 in 10 mL of MEM). The virus titer was $3 \times 10^6$ per mL. Also, 200 ul of HSV-2 was added to each compartment of the lower half of each plate. HSV-2 was diluted 1:2,000 (5.0 ul of stock HSV-2 in 10 mL of MEM). The virus titer was $6 \times 10^5$ per mL.

3. The plates were incubated at 37° C. for four hours.

4. The inoculum was removed and one mL of the MEM containing drugs # 1–4 was added to the four compartments.

TABLE 8

| Concentrate | 1:20 | 1:40 | 1:80 | 1:160 | 1:320 |
|---|---|---|---|---|---|
| Drug (ul) | 400 | 200 | 100 | 50 | 25 |
| MEM (ul) | 3600 | 3800 | 3900 | 3950 | 3975 |

5. Results: HSV-1, liquid overlay, drugs added immediately after virus absorption.

TABLE 9

Drug #1B - HSV 1 Test Results

| Concentration | 1:20 | 1:40 | 1:80 | 1:160 | 1:320 |
|---|---|---|---|---|---|
| plaques | 37 | toxic | toxic | toxic | 15?* |
| plaques | 45 | | | | 18?* |
| Average | 41 | | | $IC_{50}$ | |

Comments: Slightly toxic, test was difficult to read.

HSV-2, liquid overlay, drugs added immediately after virus absorption.

TABLE 10

Drug #1B - HSV 2 Test Results

| Concentration | 1:20 | 1:40 | 1:80 | 1:160 | 1:320 |
|---|---|---|---|---|---|
| plaques | 38 | toxic | toxic | toxic | 21 |
| plaques | 42 | | | | 17 |
| Average | 40 | | | | 19 $IC_{50} > 1:320$ |

Comments: Test was too toxic to give a good reading.

TABLE 11

Drug #2B - HSV 1 Test Results

| Concentration | 1:20 | 1:40 | 1:80 | 1:160 | 1:320 |
|---|---|---|---|---|---|
| plaques | 39 | 2* | 8* | 23* | 24 | 44 |
| plaques | 40 | 3 | 18 | 11 | 28 | 38 |
| Average | 40 | 3 | 13 | 17 | 26 | $IC_{50} > 1:80$ |

Comments: Small plaques.

TABLE 12

Drug #2B - HSV 2 Test Results

| Concentration | 1:20 | 1:40 | 1:80 | 1:160 | 1:320 |
|---|---|---|---|---|---|
| plaques | 48 | 21 | 33 | | |
| plaques | 52 | 22 | 38 | | |
| Average | 50 | 21.5 | 35.5 | | $IC_{50} > 1:20$ |

TABLE 13

Drug #3B - HSV 1 Test Results

| Concentration | 1:20 | 1:40 | 1:80 | 1:160 | 1:320 |
|---|---|---|---|---|---|
| plaques | 44 | 1* | 17 | 31 | 37 |
| plaques | 46 | — | 16 | 28 | 27 |
| Average | 45 | — | 17 | 30 | 32 $IC_{50} > 1:40$ |

Comments: Although there was some toxicity, drug very successful there did not appear to be any plaques.

TABLE 14

Drug #3B - HSV 2 Test Results

| Concentration | 1:20 | 1:40 | 1:80 | 1:160 | 1:320 |
|---|---|---|---|---|---|
| few cells | | 11* | 27 | 30 | 35 |
| plaques | 44 | 10 | 32 | | |
| Average | 44 | 11 | 29.5 | | $IC_{50} > 1:20$ |

Comments: A difficult test to get a really good reading. However the drug has successful inhibitory activity.

TABLE 15

Drug #4B - HSV 1 Test Results

| Concentration | 1:40 | 1:80 | 1:160 | 1:320 | 1:640 |
|---|---|---|---|---|---|
| plaques | 47 | toxic | toxic | toxic | 33 |
| plaques | 48 | | | 28 | |
| Average | 48 | | | 30 | $IC_{50} > 1:320$ |

Comments: Too toxic at the higher levels. Nonetheless, there was inhibitory activity at 1:320

TABLE 16

Drug #4B - HSV 2 Test Results

| Concentration | 1:40 | 1:80 | 1:160 | 1:320 | 1:640 |
|---|---|---|---|---|---|
| plaques | 38 | toxic | toxic | toxic | 2* | 16 |
| plaques | 40 | | | | 4 | 20 |
| Average | 39 | | | | 3 | 18 $IC_{50} > 1:640$ |

Comments: Toxicity probably due to the benzalkonium chloride. The drug at the 1:320 dilution showed very strong inhibitory activity.

The in vitro tests of Examples 21–24 used raw materials which were not refined. Nevertheless, the tests demonstrate surprisingly good viral inhibitory activity and a probable synergy between the constituents.

In the preceding in vitro tests where Drugs #3, 3A and 3B, were *Echinacea purpurea* phytochemicals extracted and combined with benzalkonium chloride surfactant, the resultant medicine, demonstrated the greater antiviral activity, and most remarkably demonstrated a synergy between the components: *Echinacea purpurea* and benzalkonium chloride. This can possibly be explained by a shared stability and enhanced reactivity between the two components. The benzalkonium chloride in the synergistic mixture exhibited a lesser degree of toxicity and the synergistic combination (medicine) exhibited a greater degree of antiviral activity, particularly with HSV-2.

HIV Tests

Viracea-1 and Viracea-2 were tested for evaluation of anti-HIV activity in acute infection model assays. Additional assays were performed to evaluate the range and mechanism of action of the two compounds.

Compounds Viracea-1 and Viracea-2 were supplied as solutions. Formulation included filtering of the solution and centrifugation. The high test concentration used in each assay varied from a 1:5 dilution to a 1:100 dilution in tissue culture medium. Each compound was stored at 70° C. prior to use. In these tests, the following drugs (composition) were used.

*Viracea* 1 =

*Viracea* 2 =

Propagation and Quantitation of Cell Lines and Virus Stocks

Cells utilized in the compound screening assays were designated as the CEM-SS cell line. These cells are highly susceptible to infection with HIV, rapidly form multinucleated syncytia, and are eventually killed by HIV. These cells are easily maintained ($2-7 \times 10^3$ cells per ml) in RPMI 1640 tissue culture medium supplemented with 10% fetal bovine serum, glutamine, and antibiotics. The cells are passaged twice weekly at 1:20 dilution. Passage number is logged each week and the cells are discarded after twenty weeks of passage and fresh CEM-SS cells are thawed and utilized in the assay. Stocks of CEM-SS cells have been frozen in liquid nitrogen in 1 ml NUNC vials in 90% fetal calf serum and 10% dimethyl sulfoxide (DMSO). Following thawing, CEM-SS cells are routinely ready to be utilized in the primary screen assay after two weeks in culture. Prior to replacing a late passage cell line, the new CEM-SS cells are tested in the screening assay protocol utilizing the current stock of infectious virus and AZT. If the infectivity of the virus is significantly different on the new cells or if AZT appears less active than expected the new cells will not be entered into the screening program. Mycoplasma testing is routinely performed on all cell lines (see above).

Virus pools are prepared and titrated in CEM-SS cells, placed in 5 ml aliquots, and frozen at −135° C. After thawing, unused virus is discarded to avoid changes in infectious titer. Optimization assays have documented a one-log reduction in virus titer upon the first freeze-thaw cycle, and less drastic titer reduction with subsequent rounds of freeze-thaw. Virus pools are prepared by the acute infection of $5 \times 10^5$ CEM-SS cells with HIV in a volume of 200 µl at a multiplicity of infection determined to give complete cell killing at day 7 post-infection (approximately 0.05 for the $III_B$ isolate of HIV-1 and 0.01 for the RF isolate of HIV-1). Infection is allowed to proceed for one hour at 37° C. and then the cells are transferred to a T25 flask and the volume is increased to 2 ml. On day 1 post-infection the volume is brought to 5 ml and on day 2 the volume is increased to 10 ml. Beginning on day 4, the cells are pelleted, the supernatant is saved and the cells are resuspended in a fresh 10 ml aliquot of tissue culture medium. Complete medium changes on a daily basis, rather than allowing growth of the cells in the medium for longer periods of time, allows the virus inoculum utilized in the primary screen to remain relatively undepleted of nutrients when it is used to infect cells. The staining reaction utilized (XTT) requires that the glucose concentration remain high. Wells depleted of glucose by cell growth will not permit metabolic conversation of the tetrazolium dye to the formazan product.

Cell-free supernatants from the acutely infected cells are saved on day 4, day 5, day 6, and day 7. An aliquot of supernatant is saved separately on each day for use in titer determination. Titer determinations include reverse transcriptase activity assay, endpoint titration or plaque assay (CEM-SS) quantitation of infectious particles, and quantitation of cell killing kinetics. It has been determined that peak levels of infectious virus are produced in the acutely infected cultures as the viability of the cells falls through the 50% level. Since the primary screening assay quantifies the protective effects of a compound by its ability to inhibit HIV-induced cytopathic effects, the quantity of virus required to kill CEM-SS cells in 6 days is routinely utilized to determine the amount of virus required per well in the primary screening assay. Each of the daily pools is titrated in the primary screening XTT assay protocol by performing two-fold dilutions of the virus beginning at a high test concentration of 50 µl of virus per well. The tetrazolium dye XTT staining method is utilized to determine the exact amount of virus required to kill all the CEM-SS cells in each well and this minimum amount of virus is utilized for performance of all primary testing. Identical methods are utilized to prepare all virus isolates utilized in the laboratory, including laboratory derived strains of HIV-1, HIV-2 and STV. Clinical isolates utilized are passaged in fresh human cells and the methods for the growth of these cells and the production of virus pools is described below.

Microtiter Antiviral XTT Assay

Cell Preparation

CEM-SS cells or other established human cell line used in these experiments were passaged in T-150 flasks for use in the assay. On the day preceding the assay, the cells were split 1:2 to assure they would be in an exponential growth phase at time of infection. On the day of assay the cells were washed twice with tissue culture medium and resuspended in fresh tissue culture medium. Total cell and viability counting was performed using a hemacytometer and trypan blue dye exclusion. Cell viability was greater than 95% for the cells to be utilized in the assay. The cells were pelleted and resuspended at $2.5 \times 10^4$ cells per ml in tissue culture medium. Cells were added to the drug-containing plates in a volume of 50 µl.

Virus Preparation

A pretitered aliquot of virus was removed from the freezer (−80° C.) and allowed to thaw slowly to room temperature in a biological safety cabinet. The virus was resuspended and diluted into tissue culture medium such that the amount of virus added to each wall in a volume of 50 µl will be the amount determined to give complete cell killing at 6 days post-infection. In general the virus pools produced with the IIIB isolate of HIV required the addition of 5 µl of virus per well. Pools of RF virus were five to ten fold more potent, requiring 0.5–1 µl per well. $TCID_{50}$ calculation by endpoint titration in CEM-SS cells indicated that the multiplicity of infection of these assays ranged from 0.005–2.5.

Plate Format

The format of the test plate has been standardized and contained cell control wells (cells only), virus control wells (cells plus virus), drug toxicity control wells (cells plus drug only), drug colorimetric control wells (drug only) as well as experimental wells (drug plus cells plus virus).

EXAMPLES 25–48

XTT Staining of Screening Plates

After 6 days of incubation at 37° C. in a 5% $CO_2$ incubator the test plates were analyzed by staining with the tetrazolium dye XTT. XTT-tetrazolium is metabolized by the mitochondrial enzymes of metabolically active cells to a soluble formazan product, allowing the rapid quantitative analysis of the inhibition of HIV-induced cell killing by anti-HIV test substances. On day 6 post-infection plates were removed from the incubator and observed. The use of round bottom microtiter plates allows rapid macroscopic analysis of the activity of a given test compound by the evaluation of pellet size. The results of the macroscopic observations were confirmed and enhanced by further microscopic analysis. XTT solution was prepared only as a stock of 1 mg/ml in PBS. Phenazine methosulfate (PMS) solution was prepared at 15 mg/ml in PBS and stored in the dark at −20° C., XTT/PMS stock was prepared immediately before use by diluting the PMS 1:100 into PBS and adding 40 µl per ml of XTT solution. Fifty microliters of XTT/PMS was added to each well of the plate and the plate was reincubated for 4 hours at 37° C. Adhesive plate sealers were used in place of the lids, the sealed plate was inverted several times to mix the soluble formazan product and the plate was read spectrophotometrically at 450 nm with a Molecular Devices Vmax plate reader. Using a % CPE Reduction, % Cell Viability, $IC_{25,\ 50\ \&\ 95}$, $TC_{25,\ 50\ \&\ 95}$ and other indices were calculated.

TABLE 17

IN VITRO ANTIVIRAL RESULTS XTT ASSAY FOR VIRACEA 1

| 1 | 2 | 3 | 4 | 5 | 6 | 7 | 8 | 9 | 10 | 11 | 12 |
|---|---|---|---|---|---|---|---|---|---|---|---|
| Reagent Background | | | | | | Plastic Background | | | | | |
| 0.169 | 0.160 | 0.160 | 0.159 | 0.154 | 0.167 | 0.066 | 0.063 | 0.058 | 0.061 | 0.063 | 0.067 |
| Tox | cc/vc | Experimental High Conc. | | | Tox | Tox | Experimental Low Conc. | | | cc/vc | Tox |
| 1.498 | 1.461 | 0.196 | 0.378 | 0.278 | 1.466 | 1.474 | 0.204 | 0.211 | 0.208 | 1.517 | 1.511 |
| 1.392 | 1.461 | 0.192 | 0.196 | 0.293 | 1.414 | 1.479 | 0.205 | 0.247 | 0.185 | 1.496 | 1.497 |
| 1.333 | 1.426 | 0.318 | 1.410 | 1.372 | 1.356 | 1.482 | 0.242 | 0.182 | 0.215 | 1.478 | 1.519 |
| 1.208 | 0.219 | 1.134 | 1.181 | 1.110 | 1.206 | 1.487 | 0.219 | 0.208 | 0.215 | 0.189 | 1.512 |
| 1.032 | 0.193 | 0.940 | 0.828 | 0.968 | 0.944 | 1.480 | 0.192 | 0.207 | 0.254 | 0.309 | 1.506 |
| 0.656 | 0.222 | 0.596 | 0.582 | 0.544 | 0.572 | 1.464 | 0.206 | 0.254 | 0.186 | 0.184 | 1.468 |
| Colorimetric Background-High Concentrations | | | | | | Colormetric Background-Low Concentrations | | | | | |
| 0.289 | 0.182 | 0.168 | 0.171 | 0.166 | 0.167 | 0.163 | 0.173 | 0.172 | 0.166 | 0.164 | 0.180 |

TABLE 18

VIRACEA 1

| STRN | RF | | | | |
|---|---|---|---|---|---|
| Reagent | 0.62 | Drug Viracea 1 | 25% | 50% | 95% |
| Virus Control | 0.058 | TC | 1:66 | 1:18.5 | 1:10 |
| Cell Control | 1.312 | IC | | 1:625 | 1:400 |
| Differential | 1.254 | Antiviral Index (AJ) | | 9.47 | 21.6 |

TABLE 19

VIRACEA 1

| | Drug Viracea 1 | | Antiviral Test Values | | Cytotoxicity Test Values | | |
|---|---|---|---|---|---|---|---|
| | Row on Plate | Conc. (um) | Mean O.D. | % Red in Viral CPE | Mean O.D | % Cell Viability | Colorimetric Control |
| Based on | Low B | 0.00003 | −.030 | 0% | 1.313 | 100% | 0.018 |
| values of | C | 0.0001 | −.010 | 0% | 1.324 | 100% | 0.003 |
| columns | D | 0.00032 | −.011 | 0% | 1.334 | 100% | 0.005 |
| 7 through 12 | E | 0.001 | −.015 | 0% | 1.328 | 100% | 0.010 |
| (right side | F | 0.0032 | −.013 | 0% | 1.321 | 100% | 0.011 |
| of plate) | G | 0.01 | −.006 | 0% | 1.303 | 99% | 0.002 |
| Based on | B | 0.032 | 0.059 | 5% | 1.315 | 100% | 0.006 |
| values of | C | 0.1 | 0.003 | 0% | 1.237 | 94% | 0.005 |
| columns | D | 0.32 | 0.804 | 64% | 1.173 | 89% | 0.010 |
| 1 through 6 | E | 1 | 0.915 | 73% | 1.039 | 79% | 0.007 |
| (left side | F | 3.2 | 0.673 | 54% | 0.807 | 62% | 0.020 |
| of plate) high | G | 10 | 0.228 | 18% | 0.326 | 25% | 0.127 |

TABLE 20

IN VITRO ANTIVIRAL RESULTS XTT ASSAY FOR VIRACEA 2

| 1 | 2 | 3 | 4 | 5 | 6 | 7 | 8 | 9 | 10 | 11 | 12 |
|---|---|---|---|---|---|---|---|---|---|---|---|
| Reagent Background | | | | | | Plastic Background | | | | | |
| 0.169 | 0.163 | 0.164 | 0.166 | 0.160 | 0.170 | 0.074 | 0.072 | 0.067 | 0.067 | 0.067 | 0.068 |
| Tox | cc/vc | Experimental High Conc. | | | Tox | Tox | Experimental Low Conc. | | | cc/vc | Tox |
| 1.468 | 1.421 | 0.461 | 0.257 | 1.170 | 1.467 | 1.501 | 0.207 | 0.222 | 0.214 | 1.506 | 1.503 |
| 1.321 | 1.397 | 1.316 | 0.209 | 0.191 | 1.340 | 1.494 | 0.200 | 0.202 | 0.204 | 1.446 | 1.487 |
| 0.906 | 1.345 | 0.249 | 0.764 | 0.836 | 0.953 | 1.485 | 0.227 | 0.179 | 0.179 | 1.453 | 1.500 |
| 0.219 | 0.256 | 1.190 | 0.207 | 0.210 | 0.234 | 1.491 | 0.204 | 0.190 | 0.228 | 0.192 | 1.506 |

TABLE 20-continued

IN VITRO ANTIVIRAL RESULTS XTT ASSAY FOR VIRACEA 2

| 1 | 2 | 3 | 4 | 5 | 6 | 7 | 8 | 9 | 10 | 11 | 12 |
|---|---|---|---|---|---|---|---|---|---|---|---|
| Reagent Background | | | | | | Plastic Background | | | | | |
| 0.169 | 0.163 | 0.164 | 0.166 | 0.160 | 0.170 | 0.074 | 0.072 | 0.067 | 0.067 | 0.067 | 0.068 |
| Tox | cc/vc | Experimental High Conc. | | | Tox | Tox | Experimental Low Conc. | | | cc/vc | Tox |
| 0.168 | 0.190 | 0.161 | 0.161 | 0.148 | 0.157 | 1.503 | 0.237 | 0.195 | 0.202 | 0.186 | 1.501 |
| 0.242 | 0.223 | 0.238 | 0.239 | 0.230 | 0.242 | 1.495 | 0.201 | 0.204 | 0.227 | 0.189 | 1.503 |
| Colormetric Background-High Concentrations | | | | | | Colorimetric Background-Low Concentrations | | | | | |
| 0.258 | 0.172 | 0.159 | 0.165 | 0.163 | 0.165 | 0.165 | 0.166 | 0.166 | 0.171 | 0.159 | 0.169 |

TABLE 21

VIRACEA 2

| STRN | RF | | | | | |
|---|---|---|---|---|---|---|
| Regent | 0.165 | Drug Viracea 2 | 25% | 50% | 95% | |
| Virus Control | 0.041 | TC | 1:450 | :250 | 1:100 | |
| Cell Control | 1.263 | IC | 1:900 | | | |
| Differential | 1.222 | Antiviral Index (AI) | 2.02 | | | |

TABLE 22

VIRACEA 2

| Drug Viracea 2 | | | Antiviral Test Values | | Cytotoxicity Test Values | | |
|---|---|---|---|---|---|---|---|
| | Row on Plate | Conc. (um) | Mean O.D. | % Red in Viral CPE | Mean O.D | % Cell Visibility | Colorimetric Control |
| Based on | Low B | 0.00003 | 0.004 | 0% | 1.335 | 100% | 0.004 |
| values of | C | 0.0001 | 0.002 | 0% | 1.331 | 100% | −.006 |
| columns | D | 0.00032 | −.017 | 0% | 1.321 | 100% | 0.006 |
| 7 through 12 | E | 0.001 | 0.000 | 0% | 1.332 | 100% | 0.001 |
| (right side | F | 0.0032 | 0.004 | 0% | 1.336 | 100% | 0.001 |
| of plate) | G | 0.01 | 0.005 | 0% | 1.334 | 100% | 0.000 |
| Based on | B | 0.032 | 0.090 | 7% | 1.302 | 100% | 0.000 |
| values of | C | 0.1 | 0.368 | 30% | 1.167 | 92% | −.002 |
| columns | D | 0.32 | 0.410 | 34% | 1.764 | 61% | 0.000 |
| 1 through 6 | E | 1 | 0.002 | 0% | 1.067 | 5% | −.006 |
| (left side | F | 3.2 | −.056 | 0% | −.010 | 0% | 0.007 |
| of plate) | High G | 10 | −.063 | 0% | −.016 | 0% | 0.093 |

EXAMPLES 49–54

Reverse Transcriptase Activity Assay

A microtiter based reverse transcriptase (RT) reaction was utilized. Tritiated thymidine triphosphate (NEN) (TTP) was resuspended in distilled $H_2O$ at 5 Ci/ml. Poly rA and oligo dT were prepared as a stock solution which was kept at −20° C. The RT reaction buffer was prepared fresh on a daily basis and consists of 125 µl 1MEGTA, 125 µl $dH_2O$, 125 µl Triton X-100, 50 µl 1M Tris (pH 7.4), 50 µl 1MDTT, and 40 µl $1MMgCl_2$. These three solutions were mixed together in a ratio of 1 parts TTP, 2.5 parts poly rA:oligo dT, 2.5 parts reaction, the reaction buffer and 4 parts distilled water. Ten microliters of this reaction mixture was placed in a round bottom microtiter plate and 15 µl of virus containing supernatant was added and mixed. The plate was incubated at 37° C. and incubated for 60 minutes. Following reaction, the reaction volume was spotted onto filter mats, washed 6 times for 5 minutes each in a 5% sodium phosphate buffer, 2 times for 1 minute each in distilled water, 2 times for 1 minute each in 70% ethanol, and then dried. The dried filter mat was placed in a plastic sample bag. Betaplate scintillation fluid was added and the bag was heat sealed. Incorporated radioactivity was quantitated utilizing a Wallac Microbeta scintillation counter.

TABLE 23

VIRACEA-1: PBMC/ROJO REVERSE TRANSCRIPTASE ACTIVITY

| Conc. | 1:0 | 1:100,000 | 1:32,000 | 1:10,000 | 1:3200 | 1:1000 | 1:320 | 1:100 | 1:32 | 1:10 |
|---|---|---|---|---|---|---|---|---|---|---|
| Sample 1 | 28139 | 31490 | 35838 | 42526 | 39967 | 38024 | 20042 | 12715 | 415 | 1742 |
| Sample 2 | 24587 | 35989 | 35757 | 32780 | 34191 | 25895 | 16677 | 7587 | 12495 | 12513 |

TABLE 23-continued

VIRACEA-1: PBMC/ROJO
REVERSE TRANSCRIPTASE ACTIVITY

| Conc. | 1:0 | 1:100,000 | 1:32,000 | 1:10,000 | 1:3200 | 1:1000 | 1:320 | 1:100 | 1:32 | 1:10 |
|---|---|---|---|---|---|---|---|---|---|---|
| Sample 3 | 32527 | 34334 | 34782 | 31899 | 43755 | 34038 | 28838 | 10896 | 4251 | 7551 |
| Sample 4 | 28418 | 33938 | 35459 | 35768 | 39304 | 32652 | 21852 | 10399 | 5720 | 7269 |
| % VC | 100.0 | 119.4 | 124.8 | 125.9 | 138.3 | 114.9 | 76.9 | 36.6 | 20.1 | 25.6 |

TABLE 24

VIRACEA-1: PBMC/ROJO
TOXICITY VALUES

| Conc. | 1:0 | 1:100,000 | 1:32,000 | 1:10,000 | 1:3200 | 1:1000 | 1:320 | 1:100 | 1:32 | 1:10 |
|---|---|---|---|---|---|---|---|---|---|---|
| Sample 1 | 2.029 | 2.167 | 2.200 | 2.137 | 1.975 | 2.025 | 0.966 | 0.764 | 0.840 | 1.033 |
| Sample 2 | 2.120 | 2.234 | 2.169 | 2.203 | 2.263 | 1.895 | 1.009 | 0.696 | 0.916 | 1.058 |
| Sample 3 | 1.879 | 2.176 | 2.160 | 2.053 | 2.038 | 1.847 | 0.916 | 0.734 | 0.768 | 1.128 |
| Sample 4 | 2.009 | 2.192 | 2.176 | 2.131 | 2.092 | 1.922 | 0.964 | 0.731 | 0.841 | 1.073 |
| % VC | 100.0 | 109.1 | 108.3 | 106.1 | 104.1 | 96.7 | 48.0 | 38.4 | 41.9 | 53.4 |

TABLE 25

VIRACEA-2: PBMC/ROJO
Reverse Transcriptase Activity

| Conc. | 1:0 | 1:100,000 | 1:32,000 | 1:10,000 | 1:3200 | 1:1000 | 1:320 | 1:100 | 1:32 | 1:10 |
|---|---|---|---|---|---|---|---|---|---|---|
| Sample 1 | 28139 | 31734 | 36488 | 34880 | 31240 | 2287 | 7436 | 463 | 96 | 38 |
| Sample 2 | 24587 | 27559 | 33120 | 23103 | 33408 | 20550 | 9478 | 265 | 103 | 81 |
| Sample 3 | 32527 | 24114 | 23828 | 28137 | 23174 | 25825 | 11132 | 309 | 77 | 55 |
| Sample 4 | 28418 | 27802 | 31145 | 26677 | 29274 | 16221 | 9349 | 346 | 92 | 58 |
| % VC | 100.0 | 97.8 | 109.6 | 100.9 | 103.0 | 57.1 | 32.9 | 1.2 | 0.3 | 0.2 |

TABLE 26

VIRACEA-2: PBMC/ROJO
TOXICITY VALUES

| Conc. | 1:0 | 1:100,000 | 1:32,000 | 1:10,000 | 1:3200 | 1:1000 | 1:320 | 1:100 | 1:32 | 1:10 |
|---|---|---|---|---|---|---|---|---|---|---|
| Sample 1 | 2.029 | 1.547 | 1.460 | 1.488 | 1.345 | 1.354 | 0.860 | 0.546 | 0.429 | 0.611 |
| Sample 2 | 2.120 | 1.503 | 1.548 | 1.622 | 1.902 | 1.489 | 0.971 | 0.529 | 0.434 | 0.627 |
| Sample 3 | 1.879 | 1.364 | 1.463 | 1.720 | 1.649 | 1.223 | 0.772 | 0.451 | 0.433 | 0.633 |
| Sample 4 | 2.009 | 1.471 | 1.490 | 1.610 | 1.632 | 1.355 | 0.868 | 0.509 | 0.432 | 0.624 |
| % VC | 100.0 | 73.2 | 74.2 | 80.1 | 81.2 | 67.5 | 43.2 | 25.3 | 21.5 | 31.0 |

ELISA

ELISA kits were purchased from Coulter. The assay is performed according to the manufacturers recommendations. Prior to ELISA analysis, the reverse transcriptase activity assays were routinely performed and the values were used for incorporated radioactivity in the RT activity assay to determine the dilution of samples required for the ELISA. Control curves were generated in each assay to accurately quantititate the amount of capsid protein in each sample. Data was obtained by spectrophotometric analysis at 450 nm using a Molecular Devices Vmax plate reader. P24 concentrations were calculated from the optical density values by use of the Molecular Devices software package Soft Max.

Infectious Particles

Infectious virus particles were quantitated utilizing the CEM-SS plaque assay and the Quantitative infectivity assay for HIV-1 and HIV-2. Flat bottom 96-well microtiter plates were coated with 50 µl of poly-L-lysine at 50 µg/ml for 2 hours at 37° C. The wells were then washed with PBS and $2.5 \times 10^5$ CEM-SS cells were placed in the microtiter well where they became fixed to the bottom of the plate. Enough cells were added to form a monolayer of CEM-SS cells in each well. Virus containing supernatant was added from each well of the XTT phase, including virus and cell controls and each serial dilution of the test substance. The number of syncytia were quantitated in the flat bottom 96-well microtiter plate with an Olympus CK2 inverted microscope at 4 days following infection. Each syncytium resulted from a single infectious HIV virion.

Anti-HIV Activity In Fresh Human Cells: Assay In Fresh Human T-lymphocytes

Fresh human peripheral blood lymphocytes (PBL) were isolated from voluntary Red Cross donors, seronegative for HIV and HBV. Leukophoresed blood is diluted 1:1 with Dulbecco's phosphate buffered saline (PBS), layered over 14 mL of Ficoll-Hypaque density gradient in a 50 mL centrifuge tube. Tubes were then centrifuged for 30 minutes at 600×.g. Banded PBLs were gently aspirated from the resulting interface and subsequently washed 2× with PBS by low speed centrifugation. After final wash, cells were enumerated by trypan blue exclusion and re-suspended at $1 \times 10^7$/mL in RPMI 1640 with 15% Fetal Bovine Serum (FBS), 2 mM L-glutamine, 4 µg/mL PHA-P and allowed to incubate for 48–72 hours at 37° C. After incubation, PBLs were centrifuged and reset in RPMI 1640 with 15% FBS, 2 mM L-glutamine, 100 U/mL penicillin, 100 µg/mL streptomycin, 10 µg/mL gentamicin, and 20 U/mL recombinant human 1L-2. PBLs were maintained in this medium at a concentration of 1–2×10E6/mL with bi-weekly medium changes, until use in the assay protocol.

For the PBL assay, PHA-P stimulated cells from at least two normal donors were pooled, set in fresh medium at 2×10E6/mL and plated in the interior wells of a 96 well round bottom microplate at 50 µL/well. Test drug dilutions were prepared at a 2× concentration in microtiter tubes and 100 µL of each concentration is placed in appropriate wells in a standard format. 50 µL of a predetermined dilution of virus stock was placed in each test well. Wells with cells and virus alone were used for virus control. Separate plates were identically set without virus for drug cytotoxicity studies using an XTT assay system.

In the standard PBL assy (MOI: 0.2), the assay was ended on day 7 following collection of cell free supernatant samples for reverse transcriptase activity assay. In the low MOI PBL assay (MOI: 0.02), supernatant samples were collected on day 6, day 11, and day 14 post-infection and analyzed for RI activity. Tritiated thymidine triphosphate (NEN) (TTP) was resuspended in distilled $H_2O$ at 5 Ci/ml. Poly rA and oligo dT were prepared as a stock solution which was kept at −20° C. The RT reaction buffer was prepared fresh on a daily basis and consists of 125 µl 1MEGTA, 125 µl $dH_2O$, 110 µl 10% SDS, 50 µl 1M Tris (pH 7.4), 50 µl IM DTT, and 40 µl 1M $MgCl_2$. These three solutions were mixed together in a ratio of 2 parts TTP, 1 part poly rA:oligo dT, and 1 part reaction buffer. Ten microliters of this reaction mixture was placed in a round bottom microtiter plate and 15 µl of virus containing supernatant was added and mixed. The plate was incubated at 37° C. in a water bath with a solid support to prevent submersion of the plate and incubated for 60 minutes. Following reaction, the reaction volume was spotted onto pieces of DE81 paper, washed 5 times for 5 minutes each in a 5% sodium phosphate buffer, 2 times for 1 minute each in distilled water, 2 times for 1 minute each in 70% ethanol, and then dried. Opti-Fluor O was added to each sample and incorporated radioactivity was quantitated utilizing a Wallac 1450 Microbetaplus liquid scintillation counter.

Tritiated thymidine incorporation was measured in parallel cultures at day 7. Each well was pulsed with 1 µCi of tritiated thymidine and the cells were harvested 18 hours later with a Skatron cell harvester onto glass fiber filter papers. The filters were dried, placed in a scintillation vial with 1 ml of scintillation cocktail and incorporated radioactivity was quantitated on a Packard Tri-Carbh 1900 TR liquid scintillation counter.

EXAMPLES 55–78

Anti-HIV Activity in Fresh Human Cells: Assay in Fresh Human Monocyte Macrophages For isolation of a adherent cells, $3 \times 10^6$ non-PHA stimulated peripheral blood cells were resuspended in Hanks buffered saline with calcium and magnesium supplemented with 10% human AB serum. The cells were placed in a 24-well microtiter plate at 37° C. for 2 hours. Non-adherent cells were removed by vigorously washing six times. The adherent cells were cultured for 7 days in RPMI 1640 tissue culture medium with 15% fetal bovine serum. The cultures were carefully monitored for confluency during this incubation period. Infection of the cells was performed with the monocytotropic HIV-1 strains BaL or ADA and the matched pair of AZT-sensitive and AZT-resistant virus isolates. Each of these virus isolates was obtained from the NLAID AIDS Research and Reference Reagent Program. High titer pools of each of these viruses have been harvested from infected cultures of peripheral blood adherent cells and frozen in 1.0 ml aliquots at −80° C. Monocyte-macrophage monolayers were infected at an MOI of 0.1. Compounds to be evaluated in the monolayers were infected at an MOI of 0.1. Compounds to be evaluated in the monocyte-macrophage assay were added to the monolayers shortly before infection in order to maximize the potential for identifying active compounds.

At two days post-infection, the medium was decanted and the cultures washed twice with complete medium in order to remove excess virus. Fresh medium alone or medium containing the appropriate concentration of drugs was added and incubation continued for an additional 5 days. XTT-tetrazolium or trypan blue exclusion assays for cell viability and HIV p24 ELISA assays for production of p24 core antigen were performed on Day 7 post-infection. ELISA kits were purchased from Coulter. Control curves were generated in each assay to accurately quantitate the amount of capsid protein in each sample. Data was obtained by spectrophotometric analysis at 450 nm using a Molecular Devices Vmax plate reader. P24 concentrations were calculated from the optical density values by use of the Molecular Device software package Soft Max.

TABLE 27

| | MACROPHAGE ASSAY FOR VIRACE 1 pg/mL P-24 Activity | | | | | | |
|---|---|---|---|---|---|---|---|
| µM | AZT Control vs. ADA | | | Dilution | Viracea #1 vs. ADA | | |
| 4 | 20.94 | 27.07 | 57.73 | 1:100 | 110.1 | 46.0 | 78.9 |
| 1.28 | 3.66 | 11.46 | 35.99 | 1:312 | 145.2 | 87.3 | 143.0 |
| 0.410 | 25.96 | 20.94 | 27.07 | 1:976 | 505.4 | 126.9 | 590.1 |
| 0.131 | 28.19 | 28.19 | 57.17 | 1:3051 | 811.9 | 98.4 | 652.5 |
| 0.042 | 34.87 | 79.47 | 105.70 | 1:9536 | 129.6 | 1055.0 | 1106.0 |

TABLE 27-continued

MACROPHAGE ASSAY FOR VIRACE 1
pg/mL P-24 Activity

| μM | AZT Control vs. ADA | | | Dilution | Viracea #1 vs. ADA | | |
|---|---|---|---|---|---|---|---|
| 0.013 | 149.10 | 279.60 | 217.70 | 1:29802 | 1058.0 | 1098.0 | 1266.0 |
| 0.004 | 470.80 | 660.90 | 912.30 | 1:93132 | 1185.0 | 1067.0 | 1195.0 |
| 0.0014 | 919.00 | 1150.00 | 678.70 | 1:291038 | 1043.0 | 754.0 | 1287.0 |
| 0.0004 | 1005.00 | 1252.00 | 954.10 | 1:909494 | 1053.0 | 1035.0 | 712.7 |

TABLE 28

MACROPHAGE ASSAY FOR VIRACEA 2
pg/mL P-24 Activity

| μM | AZT Control vs. ADA | | | Dilution | Viracea #1 vs. ADA | | |
|---|---|---|---|---|---|---|---|
| 4 | 8.65 | 8.65 | 17.45 | 1:100 | 42.19 | 22.95 | 34.49 |
| 1.28 | 9.20 | 6.45 | 25.15 | 1:312 | 4.25 | 15.25 | 41.09 |
| 0.410 | 13.60 | 10.00 | 16.35 | 1:976 | 14.70 | 17.45 | 39.44 |
| 0.131 | 53.74 | 13.60 | 62.54 | 1:3051 | 63.64 | 26.25 | 48.79 |
| 0.042 | 82.89 | 72.44 | 96.63 | 1:9536 | 48.79 | 570.60 | 180.80 |
| 0.013 | 175.80 | 168.70 | 316.00 | 1:29802 | 278.60 | 243.50 | 450.80 |
| 0.004 | 914.90 | 891.20 | 499.20 | 1:93132 | 305.60 | 599.80 | 435.90 |
| 0.0014 | 821.90 | 594.80 | 983.10 | 1:291038 | 548.10 | 947.90 | 913.20 |
| 0.0004 | 1097.00 | 1160.00 | 1098.00 | 1:909494 | 814.80 | 790.60 | 820.80 |

TABLE 29

MACROPHAGE ASSAY FOR VIRACEA 1
pg/mL P-24 Activity

| μM | AZT Control vs. XTT | | | Dilution | Viracea #1 vs. XTT | | |
|---|---|---|---|---|---|---|---|
| 4 | 1.947 | 1.750 | 2.022 | 1:100 | 1.936 | 1.754 | 2.089 |
| 1.28 | 2.244 | 2.021 | 2.097 | 1:312 | 1.835 | 1.850 | 1.931 |
| 0.410 | 2.205 | 2.107 | 2.144 | 1:976 | 2.039 | 2.007 | 1.992 |
| 0.131 | 2.067 | 2.223 | 2.191 | 1:3051 | 2.040 | 1.710 | 1.903 |
| 0.042 | 2.357 | 2.175 | 2.339 | 1:9536 | 2.156 | 2.057 | 2.156 |
| 0.013 | 2.506 | 2.204 | 2.160 | 1:29802 | 2.073 | 1.573 | 1.858 |
| 0.004 | 2.372 | 2.325 | 2.191 | 1:93132 | 2.225 | 1.978 | 2.433 |
| 0.0014 | 2.558 | 2.091 | 1.884 | 1:291038 | 2.037 | 1.559 | 2.169 |
| 0.0004 | 2.037 | 2.389 | 2.166 | 1:909494 | 2.405 | 2.198 | 2.275 |

TABLE 30

MACROPHAGE ASSAY FOR VIRACEA 2
Toxicity Studies Absorbance

| μM | AZT Control vs. ADA | | | Dilution | Viracea #1 vs. ADA | | |
|---|---|---|---|---|---|---|---|
| 4 | 1.140 | 0.981 | 1.427 | 1:100 | 1.271 | 1.244 | 1.289 |
| 1.28 | 1.692 | 1.318 | 0.985 | 1:312 | 1.081 | 1.154 | 1.393 |
| 0.410 | 1.505 | 1.258 | 1.522 | 1:976 | 1.073 | 1.183 | 1.536 |
| 0.131 | 1.427 | 1.347 | 1.043 | 1:3051 | 1.482 | 1.032 | 1.518 |
| 0.042 | 1.534 | 1.725 | 1.720 | 1:9536 | 1.031 | 1.330 | 1.053 |
| 0.013 | 1.818 | 1.526 | 1.363 | 1:29802 | 1.344 | 1.449 | 1.497 |
| 0.004 | 1.578 | 1.112 | 1.034 | 1:93132 | 1.024 | 1.554 | 1.446 |
| 0.0014 | 1.386 | 1.350 | 1.133 | 1:291038 | 1.692 | 1.112 | 1.411 |
| 0.0004 | 1.451 | 1.081 | 1.342 | 1:909494 | 1.182 | 1.163 | 1.373 |

TABLE 31

ANTI-HIV MACROPHASE ASSAY (P24)
For VIRACEA #2–4
P24 Activity (pg/mL)

| Dilution | 0 | 1:909494 | 1:291038 | 1:93132 | 1:29802 | 1:9536 | 1:3051 | 1:976 | 1:312 | 1:100 |
|---|---|---|---|---|---|---|---|---|---|---|
| Sample 1 | 1366.8 | 1347 | 524.1 | 634.4 | 457.5 | 349.9 | 193.5 | 138 | 120.9 | 46.96 |
| Sample 2 | 1366.8 | 1151 | 693.8 | 782.2 | 321.5 | 228 | 271.4 | 190.2 | 4.718 | 96.46 |
| Sample 3 | 1366.8 | 1000 | 877.9 | 642.9 | 507 | 382.2 | 136.1 | 202.1 | 171.7 | 92.5 |
| Average | 1366.8 | 1166.0 | 695.6 | 686.5 | 428.7 | 320.0 | 200.3 | 176.8 | 99.1 | 78.5 |
| % VC | 100.0 | 85.3 | 51.1 | 50.2 | 31.4 | 23.4 | 14.7 | 12.9 | 7.3 | 5.8 |

TABLE 32

VIRACEA #2–4
XTT Toxicity Value (Absorbance)

| Dilution | 0 | 1:909494 | 1:291038 | 1:93132 | 1:29802 | 1:9536 | 1:3051 | 1:976 | 1:312 | 1:100 |
|---|---|---|---|---|---|---|---|---|---|---|
| Sample 1 | 3.293 | 3.85 | 3.606 | 3.787 | 3.693 | 3.657 | 2.927 | 3.134 | 3.131 | 3.393 |
| Sample 2 | 3.293 | 3.005 | 3.662 | 3.542 | 3.685 | 3.828 | 3.408 | 2.833 | 3.074 | 3.263 |
| Sample 3 | 3.293 | 3.457 | 3.648 | 2.59 | 2.808 | 2.558 | 2.735 | 2.932 | 2.892 | 3.345 |
| Average | 3.293 | 3.437 | 3.639 | 3.306 | 3.395 | 3.348 | 3.023 | 2.966 | 3.032 | 3.334 |
| % CC | 100.0 | 104.4 | 110.5 | 100.4 | 103.1 | 101.7 | 91.800 | 90.1 | 92.1 | 101.2 |

TABLE 33

ANTI-HIV MACROPHASE ASSAY (P24)
For VIRACEA #2–5
P24 Activity (pg/mL)

| Dilution | 0 | 1:909494 | 1:291038 | 1:93132 | 1:29802 | 1:9536 | 1:3051 | 1:976 | 1:312 | 1:100 |
|---|---|---|---|---|---|---|---|---|---|---|
| Sample 1 | 1298.2 | 1350 | 793.9 | 1001 | 515.9 | 274 | 196.3 | 65.8 | 16.28 | 3.904 |
| Sample 2 | 1298.2 | 1350 | 858.6 | 851 | 780.4 | 393.3 | 102.9 | 110.2 | 38.79 | 16.28 |
| Sample 3 | 1298.2 | 1454 | 1262 | 801.2 | 837.8 | 396.1 | 222.2 | 113.1 | 42.73 | 15.72 |
| Average | 1298.2 | 1384.7 | 971.5 | 884.4 | 711.4 | 354.5 | 173.8 | 96.4 | 32.6 | 12.0 |
| % VC | 100.0 | 106.7 | 74.8 | 68.1 | 54.8 | 27.3 | 13.4 | 7.4 | 2.5 | 0.9 |

TABLE 34

VIRACEA #2–5
XTT Toxicity Value (Absorbance)

| Dilution | 0 | 1:909494 | 1:291038 | 1:93132 | 1:29802 | 1:9536 | 1:3051 | 1:976 | 1:312 | 1:100 |
|---|---|---|---|---|---|---|---|---|---|---|
| Sample 1 | 3.139 | 3.459 | 3.568 | 3.567 | 3.634 | 3.562 | 3.134 | 3.311 | 3.171 | 2.974 |
| Sample 2 | 3.139 | 3.018 | 3.295 | 3.505 | 3.533 | 3.359 | 2.833 | 3.313 | 3.133 | 2.909 |
| Sample 3 | 3.139 | 3.21 | 3.261 | 3.263 | 3.297 | 3.051 | 2.932 | 2.829 | 3.151 | 3.35 |
| Average | 3.139 | 3.228 | 3.375 | 3.445 | 3.488 | 3.312 | 2.966 | 3.151 | 3.152 | 3.078 |
| % CC | 100.0 | 102.9 | 107.5 | 109.7 | 111.1 | 105.5 | 91.8 | 100.4 | 100.4 | 98.0 |

TABLE 35

IN VITRO ANTI-HIV MACROPHASE ASSAY
For VIRACEA 1
P24 (pg/mL)

| Dilution | 0 | 1:909494 | 1:291038 | 1:93132 | 1:29802 | 1:9536 | 1:3051 | 1:976 | 1:312 | 1:100 |
|---|---|---|---|---|---|---|---|---|---|---|
| Sample 1 | 1171.0 | 712.7 | 1287.0 | 1196.0 | 1266.0 | 1106.0 | 652.5 | 590.1 | 143.0 | 78.9 |
| Sample 2 | 1171.0 | 1035.0 | 754.0 | 1067.0 | 1098.0 | 1055.0 | 98.4 | 126.9 | 87.3 | 46.0 |
| Sample 3 | 1171.0 | 1053.0 | 1043.0 | 1185.0 | 1058.0 | 129.6 | 811.9 | 505.4 | 145.2 | 110.1 |
| Average | 1171.0 | 933.6 | 1028.0 | 1149.0 | 1140.7 | 763.5 | 520.9 | 407.5 | 125.2 | 78.3 |
| % VC | 100.0 | 79.7 | 87.8 | 98.1 | 97.4 | 65.2 | 44.5 | 34.8 | 10.7 | 6.7 |

TABLE 36

VIRACEA 1
XTT Toxicity Value (Absorbance)

| Dilution | 0 | 1:909494 | 1:291038 | 1:93132 | 1:29802 | 1:9536 | 1:3051 | 1:976 | 1:312 | 1:100 |
|---|---|---|---|---|---|---|---|---|---|---|
| Sample 1 | 2.275 | 2.275 | 2.169 | 2.433 | 1.856 | 2.156 | 1.903 | 1.992 | 1.931 | 2.089 |
| Sample 2 | 2.275 | 2.198 | 1.559 | 1.978 | 1.573 | 2.057 | 1.710 | 2.007 | 1.850 | 1.754 |
| Sample 3 | 2.275 | 2.405 | 2.037 | 2.225 | 2.073 | 2.156 | 2.040 | 2.089 | 1.835 | 1.936 |
| Average | 2.275 | 2.293 | 1.922 | 2.212 | 1.835 | 2.123 | 1.884 | 2.013 | 1.872 | 1.926 |
| % CC | 100.0 | 100.8 | 84.5 | 97.2 | 80.6 | 93.3 | 82.8 | 88.5 | 82.3 | 84.7 |

TABLE 37

IN VITRO ANTI-HIV MACROPHASE ASSAY
For VIRACEA 2
P24 (pg/mL)

| Dilution | 0 | 1:909494 | 1:291038 | 1:93132 | 1:29802 | 1:9536 | 1:3051 | 1:976 | 1:312 | 1:100 |
|---|---|---|---|---|---|---|---|---|---|---|
| Sample 1 | 1045.9 | 820.80 | 913.20 | 435.90 | 450.80 | 180.80 | 48.78 | 39.44 | 41.09 | 34.49 |
| Sample 2 | 1046.8 | 790.60 | 947.90 | 599.80 | 243.50 | 570.60 | 26.25 | 17.45 | 15.25 | 22.95 |
| Sample 3 | 1045.8 | 814.80 | 548.10 | 305.60 | 276.60 | 48.79 | 63.64 | 14.70 | 4.25 | 42.19 |
| Average | 1045.8 | 808.7 | 803.1 | 447.1 | 324.3 | 266.7 | 46.2 | 23.9 | 20.2 | 33.2 |
| % VC | 100.0 | 77.3 | 76.8 | 42.8 | 31.0 | 26.6 | 4.4 | 2.3 | 1.9 | 3.2 |

TABLE 38

VIRACEA 2
XTT Toxicity Value (Absorbance)

| Dilution | 0 | 1:909494 | 1:291038 | 1:93132 | 1:29802 | 1:9536 | 1:3051 | 1:976 | 1:312 | 1:100 |
|---|---|---|---|---|---|---|---|---|---|---|
| Sample 1 | 1.439 | 1.373 | 1.411 | 1.446 | 1.497 | 1.053 | 1.518 | 1.536 | 1.393 | 1.289 |
| Sample 2 | 1.439 | 1.163 | 1.112 | 1.554 | 1.494 | 1.330 | 1.032 | 1.183 | 1.154 | 1.244 |
| Sample 3 | 1.439 | 1.182 | 1.692 | 1.024 | 1.334 | 1.031 | 1.482 | 1.073 | 1.081 | 1.271 |
| Average | 1.439 | 1.239 | 1.405 | 1.341 | 1.442 | 1.138 | 1.344 | 1.264 | 1.209 | 1.268 |
| % CC | 100.0 | 86.1 | 97.6 | 93.2 | 100.2 | 78.1 | 93.4 | 87.8 | 84.0 | 88.1 |

EXAMPLES 79–90

Binding and Fusion Inhibition Assays

These assays utilized HeLa-CD4-LTR-β-galactosidase cells which employ a tat protein-induced transactivation of the β-galactrosidase gene driven by the HIV-1 long terminal repeat (LTR) promoter. The assay was used to quantitate both the binding of infectious virons to cells and cell-cell fusion events. Infected cells form syncytia which can be easily counted microscopically after incubation with X-gal. The HIV binding inhibition assay involved plating $1 \times 10^4$ HeLa-CD4-LTR-B-galactosidase cells in 200 µl in flat bottom, 96-well microtiter plates. The cells were incubated overnight, medium was removed and replaced with 100 µl of various concentrations of ISIS 5320 or control compound. One hour later 100 µl of virus-containing medium was added to each well. Cells were incubated for an additional hour and the monolayer was washed extensively to remove unbound virus and extracellular compound. At 48 hours, the cells were fixed and stained with X-gal. Blue multinuclear cells were than counted under an inverted microscope. The cell-cell fusion inhibition assay was also performed in flat bottom, 96, well microtiter plates. HeLa-CD4-LTR-β-galactosidase cells ($5 \times 10^3$) were added to each well and incubated with test compound for 1 hours prior to the additional of $5 \times 10^3$ HL2/3 cells (28). Cells were incubated for an additional 48 hours and fixed and stained with X-gal. Blue syncytia were counted microscopically. Staining of the cells was performed by fixing the cells with a solution of 1% formaldehyde and 0.2% glutaraldehyde and staining the fixed cells with 4 µM potassium ferrocyanida, 4 µM potassium ferricyanide, 2 µM $MgCl_2$ and 0.4% X-gal in PBS. Trans-activation of β-galactosidase expression was also monitored by ELISA Cell extracts were prepared by freeze-thaw and assayed for β-galactosidase activity according to the manufacturer's recommendations. The results of the ELISA were quantitated spectrophotometrically at 405 nm using a Molecular Devices Vmax microtiter plate reader.

TABLE 39

Beta-gal Fusion Assay: Viracea #1/SK1
Number of Blue Cells per Well

| Dilution | 0 | 1:3200 | 1:1000 | 1:320 | 1:100 | 1:32 | 1:10 |
|---|---|---|---|---|---|---|---|
| Sample 1 | 49.0 | 10.0 | 11.0 | 19.0 | 4.0 | 6.0 | 3.0 |
| Sample 2 | 32.0 | 15.0 | 10.0 | 4.0 | 5.0 | 5.0 | 8.0 |
| Sample 3 | 59.0 | 15.0 | 10.0 | 5.0 | 4.0 | 4.0 | 4.0 |
| Mean | 46.7 | 13.3 | 10.3 | 9.3 | 4.3 | 5.0 | 5.0 |
| % VC | 100.0 | 28.6 | 22.1 | 20.0 | 9.3 | 10.7 | 10.7 |
| STD DEV | 29.3 | 6.2 | 1.2 | 18.0 | 1.2 | 2.1 | 5 |

TABLE 40

Beta-gal Fusion Assay: Viracea #1/SK1
PERCENT TOXICITY

| Dilution | 0 | 1:3200 | 1:1000 | 1:320 | 1:100 | 1:32 | 1:10 |
|---|---|---|---|---|---|---|---|
| Sample 1 | 1.596 | 1.574 | 1.931 | 1.925 | 1.34 | 1.576 | 1.63 |
| Sample 2 | 1.578 | 1.692 | 1.734 | 1.728 | 2.152 | 1.633 | 1.711 |
| Sample 3 | 1.66 | 1.38 | 1.811 | 1.646 | 1.647 | 1.308 | 1.545 |
| Mean | 1.612 | 1.649 | 1.825 | 1.768 | 1.946 | 1.672 | 1.629 |
| % Viability | 100.0 | 96.1 | 113.2 | 109.6 | 120.7 | 103.07 | 101.0 |

TABLE 41

Beta-gal Fusion Assay: Viracea #2/SK1
Number of Blue Cells per Well

| Dilution | 0 | 1:3200 | 1:1000 | 1:320 | 1:100 | 1:32 | 1:10 |
|---|---|---|---|---|---|---|---|
| Sample 1 | 49.0 | 26.0 | 16.0 | 17.0 | 10.0 | 2.0 | 1.0 |
| Sample 2 | 32.0 | 18.0 | 16.0 | 11.0 | 3.0 | 2.0 | 0.0 |
| Sample 3 | 59.0 | 19.0 | 20.0 | 14.0 | 5.0 | 3.0 | 1.0 |
| Mean | 46.7 | 21.0 | 17.3 | 14.0 | 6.0 | 2.3 | 0.7 |
| % VC | 100.0 | 45.0 | 37.1 | 30.0 | 12.8 | 5.0 | 1.4 |
| STD DEV | 29.3 | 9.3 | 4.9 | 6.4 | 7.7 | 1.2 | 1.2 |

TABLE 42

Beta-gal Fusion Assay: Viracea #2/SK2
PERCENT TOXICITY

| Dilution | 0 | 1:3200 | 1:1000 | 1:320 | 1:100 | 1:32 | 1:10 |
|---|---|---|---|---|---|---|---|
| Sample 1 | 1.441 | 1.59 | 1.965 | 1.972 | 1.799 | 1.932 | 0.829 |
| Sample 2 | 1.5 | 1.543 | 1.83 | 1.835 | 1.897 | 1.386 | 0.882 |
| Sample 3 | 1.425 | 1.536 | 1.839 | 1.867 | 2.036 | 1.615 | 0.758 |
| Mean | 1.455 | 1.558 | 1.875 | 1.891 | 1.911 | 1.644 | 0.823 |
| % Viability | 100.0 | 106.9 | 129.0 | 130.0 | 131.3 | 113.0 | 56.6 |

TABLE 43

Beta-gal Fusion Assay: Viracea #1
Number of Blue Cells per Well

| Conc. | 0 | 1:3200 | 1:1000 | 1:320 | 1:100 | 1:32 | 1:10 |
|---|---|---|---|---|---|---|---|
| Sample 1 | 38.0 | 37.0 | 47.0 | 37.0 | 42.0 | 55.0 | 18.0 |
| Sample 2 | 48.0 | 34.0 | 75.0 | 37.0 | 37.0 | 50.0 | 14.0 |
| Sample 3 | 32.0 | 41.0 | 48.0 | 52.0 | 57.0 | 64.0 | 9.0 |
| Mean | 39.3 | 37.3 | 56.7 | 42.0 | 45.3 | 56.3 | 13.7 |
| % VC | 100.0 | 94.9 | 144.1 | 106.8 | 115.3 | 143.2 | 34.7 |
| STD DEV | 20.5 | 8.9 | 40.4 | 22.0 | 26.2 | 18.0 | 11.5 |

TABLE 44

Beta-gal Fusion Assay: Viracea #1
PERCENT TOXICITY

| Conc. | 0 | 1:3200 | 1:1000 | 1:32 | 1:100 | 1:32 | 1:10 |
|---|---|---|---|---|---|---|---|
| Sample 1 | 1.425 | 1.951 | 1.981 | 1.815 | 1.796 | 1.639 | 1.644 |
| Sample 2 | 1.5 | 1.971 | 1.983 | 1.826 | 1.833 | 1.845 | 1.547 |
| Sample 3 | 1.441 | 1.913 | 1.942 | 1.835 | 1.823 | 1.932 | 1.644 |
| Mean | 1.455 | 1.945 | 1.969 | 1.825 | 1.817 | 1.872 | 1.612 |
| % Viability | 100.0 | 133.6 | 135.3 | 125.4 | 124.9 | 126.6 | 110.7 |

TABLE 45

Beta-gal Fusion Assay: Viracea #2
Number of Blue Cells per Well

| Conc. | 0 | 1:3200 | 1:1000 | 1:320 | 1:100 | 1:32 | 1:10 |
|---|---|---|---|---|---|---|---|
| Sample 1 | 38.0 | 64.0 | 50.0 | 56.0 | 40.0 | 50.0 | 0.0 |
| Sample 2 | 48.0 | 56.0 | 77.0 | 54.0 | 53.0 | 54.0 | 0.0 |
| Sample 3 | 32.0 | 44.0 | 46.0 | 42.0 | 48.0 | 47.0 | 0.0 |
| Mean | 39.3 | 54.7 | 57.7 | 50.7 | 47.0 | 50.3 | 0.0 |
| % VC | 100.0 | 139.0 | 146.6 | 128.8 | 119.5 | 128.0 | 0.0 |
| STD DEV | 20.5 | 25.6 | 42.9 | 19.3 | 16.7 | 8.9 | 0.0 |

TABLE 46

Viracea #2
PERCENT TOXICITY

| Conc. | 0 | 1:3200 | 1:1000 | 1:320 | 1:100 | 1:32 | 1:10 |
|---|---|---|---|---|---|---|---|
| Sample 1 | 1.425 | 1.998 | 1.87 | 1.85 | 1.592 | 0.956 | 0.174 |
| Sample 2 | 1.5 | 1.911 | 1.959 | 1.904 | 1.645 | 0.988 | 0.174 |
| Sample 3 | 1.441 | 1.976 | 1.902 | 1.939 | 1.623 | 0.965 | 0.182 |
| Mean | 1.456 | 1.962 | 1.914 | 1.898 | 1.620 | 0.970 | 0.177 |
| % Viability | 100.0 | 134.8 | 131.5 | 130.4 | 111.3 | 56.6 | 12.1 |

Topical Microbicide Assay

MEI 180 cervical epithelial cells were plated in the interior walls of a 96-well flat bottom microtiter plate at a density of 5×10 cells per well and incubated overnight. Chronically infected H9 cells wee treated with 200 μg/ml mitomycin C in complete medium for one hour, washed extensively and resuspended at 4×10$^5$ per ml. The concentration of mitomycin C used resulted in the killing of the chronically infected cells within 48 hours of treatment, allowing sufficient time for cell-cell transmission of virus to the ME-180 cells while assuring that the virus endpoint quantification would not include a contribution from the chronically infected cells. Antiviral compounds and chronically infected cells (2×10$^4$) were added to each well containing ME180 cells and incubated for 6 hours. Following co-cultivation the monolayer was washed extensively and fresh medium added. Medium was removed and fresh medium added at 24 and 48 hours post-infection to remove dead lymphocytes. On day 6 post-infection, supernatant samples were removed and analyzed for virus content by p24 ELISA.

CD4 Expression Assays

Quantitation of the effect of Viracea on CD4 expression was performed using standard flow cytometric techniques. Cells were treated with Viracea for one hour at 37° C. in tissue culture medium. Briefly, $10^6$ CEM-SS cells were incubated with or without compound for 60 minutes at room temperature. Anti-CD4 monoclonal antibody (20 μl, 3 μg/ml) (Becton-Dickinson, San Jose, Calif.) was added, and cells were incubated at 4° C. from 40 min. Cells were then washed twice with PBS, resuspended in 1° C. paraformaldehyde, and analyzed using a Becton-Dickinson FACSort flow cytometer.

Macromolecular Synthesis

CEM-SS cells were cultured in triplicate in the presence or absence of compound 24 hours at 37° C. in a humidified $CO_2$ incubator. At 24 hours, 1 μCi of [methyl-3H]-thymidine, [5-$^3$H]-uridine, or [3,4,5-$^3$H]-leucine was added to the culture and incubation was continued for an additional 8 hours. The cells were transferred to glass fiber filter papers by use of Skatron cell harvester. The glass fibers were washed with distilled water, placed in a scintillation vial and the quantity of incorporated radioactivity quantitated with a Packard Tri-Carb scintillation counter.

HIV Test Results

Viracea-1 and Viracea-2 were evaluated in the microtiter anti-HIV assay which quantifies the ability of a test compound to inhibit HIV replication and HIV-induced cell destruction. The two compounds were determined to be active against the RF strain of HIV-1 in CEM-SS cells. Viracea-1 inhibited HIV-induced cytopathic effects ($IC_{30}$) at 1:400 dilution, while Viraca-2 exhibited an $IC_2$, at a 1:900 dilution and did not reach a 50% inhibitory value. Both Viracea-1 and Viracea-2 exhibited toxicity ($TC_{30}$) to the CEM-SS cells at dilutions of approximately 1:20 and 1:250, respectively. The positive control compound, ddC, exhibited the expected level of activity against the RF virus.

Viracea-1 and Viracea-2 were evaluated for activity in fresh human PBMCs infected with the clinical HIV isolate ROJO. This low passage isolate has been defined as a drug sensitive (AZT, ddC, nevirapine) syncytium-inducing virus isolate. Neither Viracea-1 or Viracea-2 inhibited the replication of this isolate at nontoxic concentrations. Further evaluation of the compounds in PMBCs infected with ROJO were performed using IL2 stimulation of the PBMCs rather than PHA blastogenesis. Again, no activity was detected below concentrations which inhibited the growth of the PBMCs. AZT exhibited the expected level of activity in these assays.

Viracea-1 and Viracea-2 were evaluated in fresh human monocyte-macrophages infected with the low passage clinical isolate ADA. In these assays, both compounds exhibited high levels of activity with Viracea-2 being clearly superior. The 50% effective concentration of Viracea-1 and Viracea-2 was 1:4000 and 1:10000, respectively. Toxicity was not detected to the monocyte-macrophage monolayer by morphological examination or by XTT-Tetrazolium staining. AZT exhibited the expected level of activity in these assays.

Viracea-1 and Viracea-2 were found to inhibit the attachment of infectious virus to the CD4-expressing HeLa-CD4-LTR-β-galactosidase cells. Inhibition of binding of virus to the target cells was detected at dilutions of approximately 1:1000 to 1:3200 for both compounds. Neither compound had any antiviral effect on the fusion of the envelope-expressing HL2/3 cells with the HeLa-CD4-LTR-β-galactosidase cells. Toxicity was noted for both compounds in the fusion assay where compound was present for the full duration of the assay as well as with Viracea-2 in the binding assay where compound was only present for 2 hours. Chicago Sky Blue, a sulfonated dye, exhibited the expected level of activity in each of these assays.

Viracea-2 prevented the transmission of virus from chronically infected lymphocytes to the ME180 cervical epithelial cell line at a dilution of approximately 1:500 ($IC_{30}$). Toxicity was not detected in this assay to the ME180 cells. In this assay, the drug was present during the time of infection only (4 hours). Dextran sulfate (positive control, sulfated polysaccharide) and dextran (negative control) exhibited the expected level of activity in these assays.

Viracea-2 had no effect on the expression of CD4 on the cell surface.

Inhibition of the incorporation of thymidine (DNA), uridine (RNA) or leucine (protein) into high molecular weight macromolecules was observed at dilutions greater than 1:320. The inhibition of macromolecule synthesis paralleled the toxicity of the compounds in CEM-SS cells.

Summary of HIV Test Results

Viracea-1 and Viracea-2 inhibit HIV infection in established T-cells with a narrow therapeutic index. Viracea-1 and Viracea-2 potentially inhibit HIV replication in monocyte-macrophages. Viracea-1 and Viracea-2 inhibit the attachment of virus to target cells but do not prevent the fusion of infected and uninfected cells. Viracea-2 inhibits the transmission of virus in a topical microbicide assay and may be useful in the prevention of sexual transmission of HIV. Viracea-2 has no effect on cell surface CD4 expression.

Prevention and Treatment

The antimicrobial compound provides an antimicrobicide and medicine which can (1) help prevent the sexual transmission of HIV; (2) control viral load of HIV and other viruses; (3) eradicate HIV; (4) extend the latency periods of autoimmunedificiency syndrome (AIDS) in patients who have contracted HIV; (5) decrease pain and suffering of HIV patients; (6) lower the infectious spread of HIV; and (7) provide better and more successful treatment of patients with HIV. The medical treatment can also resolve the physical symptoms of an infectious outbreak of HIV, herpes simplex virus 1 or 2 (HSV 1 or HSV 2) or other infectious microbial diseases. The preceding can be accomplished by systemically applying or injecting the above described preferred antimicrobial compound (medicine) with a syringe into the rectal canal (rectum, rectal tissue, anus or anal tissue) or the vagina (vaginal tissue) of a patient infected with HIV or other infectious microbial disease for 8–12 times per day, preferably 10 times a day at intervals of every two hours, for a period of 10–18 consecutive days, preferably 14 consecutive days (two weeks) for best results. The dosage, concentration, and amount of the antimicrobial compound (medicine) can be varied depending on the severity and extent of the disease as well as the age, sex, weight, race and health of the patient. Desirably, the infected area is rinsed (washed) and dried to remove any soap or residue on the infected area before the antimicrobial compound (medicine) is applied. For treatment herpes simplex virus 1 or 2, the antimicrobial compound can be applied on the infected area, such as for 19–24 hours. Preferably, vesicular eruption of herpes virus are resolved in 19–24 hours and herpes lesions are consequently healed.

Among the many advantages of the medical treatment and medicine (compositions) of the invention are:
1. Superb treatment and prevention of HIV and other infectious diseases.
2. Superior results in ending the pain of HIV, herpes simplex viral infections and other microbial infections without toxicity.
3. Outstanding performance in rapidly resolving outbreaks of HIV, herpes simplex virus, and other microbial diseases.
4. Saves lives of newborns, children, adults and animal.
5. Reduces worldwide economic loss from HIV, herpes and other microbial diseases.
6. Resolves many of the serious emotional and mental anguish of HIV and herpes sufferers.
7. Readily available materials (ingredients).
8. Economical.
9. Safe.
10. Easy to use.
11. Dependable.
12. Effective.

Although embodiments of the invention and examples have been shown and described, it is to be understood that various modifications and substitutions, as well as rearrangements of parts, components, and process steps, methods and treatment, can be made by those skilled in the art without departing from the novel spirit and scope of this invention.

What is claimed is:

1. A method for use in treating human immunodeficiency virus, comprising the steps of:
   systemically applying an antimicrobial compound providing a medical composition into person infected with human immunodeficiency virus;
   said antimicrobial compound comprises by weight:
      from about 40% to about 60% of a phytochemical concentrate of herbaceous botanicals consisting of *Commiphora myrrha* and *Echinacea purpurea;*
      from about 20% to about 60% water providing a diluent and carrier for said phytochemical concentrate;
   systemically applying said antimicrobial compound into the person infected with human immunodeficiency virus in sufficient concentration and for a sufficient period of time to decrease human immunodeficiency virus in the person;
   controlling viral load; and
   said antimicrobial isolates of said phytochemical concentrate comprises by weight based upon the total weight of the medical composition:
      from about 0.3% to about 9% echinacoside;
      from about 0.1% to about 7% PS I is 4-O-methylglucoronoarabinoxylan, Mr 35 kD and PS II is acid rhamnoarabinogalactan, Mr 450 kD;
      from about 0.1% to about 10% cynarin;
      from about 0.2% to about 4% echinolone;
      from about 0.2% to about 8% echinacin B;
      from about 0.1% to about 6% echinaceine;
      from about 2% to about 7% anthonocyanins comprising cyananidin 3-O-B-D-glucopyranoside and 3-O-(6-O-malonyl)-B-D-glucopyranoside;
      from about 0.01% to about 0.06% pyrrolizidine alkaloids comprising tussilagine and isotussilagine;
      from about 0.003% to about 0.009% isomeric dodeca isobutyalamides and tetroenoic acid; and
   *Commophora myyrha* phytochemicals comprising members selected from the group consisting of: caryophylenes, sequiterpenes, curzerenone, dihydro fuanodien-6-one; 2-methoxyfuradine, elemol, lyndesterene, acetic acid, alpha-amyrone, arabinose, alpha-bisabolene, gamma-bisabolene, cadinene, campesterol, cholesterol, cinnamaldehyde, commiferin, alpha-commiphoric acid, beta-commiphoric acid, gamma-commiphoric acid, commiphorinic acid, m-cresol, cumic alcohol, cuminaldehyde, dipentene, 3epi-alpha-amyrin, eugenol, furanodiene, furanodienone, galactose, gum, heerabolene, alpha-heerabomyrrhol, beta-heerabomyrrhol, heeraboresene, limonene, 4-O-methyl-glucuronic acid, n-nonacesane, beta-sitosterol, and xylose.

2. A method for use in treating human immunodeficiency virus, comprising the steps of:
   systemically applying an antimicrobial compound providing a medical composition into person infected with human immunodeficiency virus;
   said antimicrobial compound comprises by weight:
      from about 40% to about 60% of a phytochemical concentrate of herbaceous botanicals consisting of *Commiphora myrrha* and *Echinacea purpurea;*
      from about 20% to about 60% water providing a diluent and carrier for said phytochemical concentrate;
   systemically applying said antimicrobial compound into the person infected with human immunodeficiency virus in sufficient concentration and for a sufficient period of time to decrease human immunodeficiency virus in the person;
   controlling viral load; and
   said antimicrobial isolates of said phytochemical concentrate comprises by weight based upon the total weight of the medical composition:
      from about 0.3% to about 9% echinacoside;
      from about 0.1% to about 7% PS I is 4-O-methylglucoronoarabinoxylan, Mr 35 kD and PS II is acid rhamnoarabinogalactan, Mr 450 kD;
      from about 0.1% to about 10% cynarin;
      from about 0.2% to about 4% echinolone;
      from about 0.2% to about 8% echinacin B;
      from about 0.1 to about 6% echinaceine;
      from about 2% to about 7% anthonocyanins comprising cyananidin 3-O-B-D-glucopyranoside and 3-O-(6-O-malonyl)-B-D-glucopyranoside;
      from about 0.01% to about 0.06% pyrrolizidine alkaloids comprising tussilagine and isoltussilagine;
      from about 0.003% to about 0.009% isomeric dodeca isobutyalamides and tetroenoic acid; and
   *Commophora myrrha* phytochemicals comprising members selected from the group consisting of: caryophylenes, sequiterpenes, curzerenone, dihydro fuanodien-6-one; 2-methoxyfuradine, elemol, lyndesterene, acetic acid, alpha-amyrone, arabinose, alpha-bisabolene, gamma-bisabolene, cadinene, campesterol, cholesterol, cinnamaldehyde, commiferin, alpha-commiphoric acid, beta-commiphoric acid, gamma-commiphoric acid, commiphorinic acid, m-cresol, cumic alcohol, cuminaldehyde, dipentene, 3-epi-alpha-amyrin, eugenol, furanodiene, furanodienone, galactose, gum, heerabolene, alpha-heerabomyrrhol, beta-heerabomyrrhol, heeraboresene, limonene, 4-O-methyl-glucuronic acid, n-nonacesane, beta-sitosterol, and xylose.

3. A method for use in treating human immunodeficiency virus in accordance with claim 2, wherein:
   said antimicrobial compound further comprises by weight from about 2% to about 12% folic acid providing a nutrient; and
   said folic acid cooperates with said *Commiphora myrrha* and said *Echinacea purpurea* to help treat human immunodeficiency virus.

4. A method for use in treating human immunodeficiency virus in accordance with claim 2, wherein said antimicrobial compound is systemically applied with a syringe into a rectal canal or vagina of a patient infected with human immunodeficiency virus.

* * * * *